United States Patent
Ueda et al.

(10) Patent No.: US 6,198,540 B1
(45) Date of Patent: Mar. 6, 2001

(54) OPTICAL COHERENCE TOMOGRAPHY HAVE PLURAL REFERENCE BEAMS OF DIFFERING MODULATIONS

(75) Inventors: Mamoru Ueda; Taisuke Hirono; Kohji Ohbayashi; Itaru Yoshizawa, all of Chofu (JP)

(73) Assignee: Kowa Company, Ltd., Aichi (JP)

( * ) Notice: Subject to any disclaimer, the term of this patent is extended or adjusted under 35 U.S.C. 154(b) by 0 days.

(21) Appl. No.: 09/402,023
(22) PCT Filed: Mar. 18, 1998
(86) PCT No.: PCT/JP98/01159
  § 371 Date: Sep. 24, 1999
  § 102(e) Date: Sep. 24, 1999
(87) PCT Pub. No.: WO98/43068
  PCT Pub. Date: Oct. 1, 1998

(30) Foreign Application Priority Data

Mar. 26, 1997 (JP) .................................................. 9-073917
Feb. 18, 1998 (JP) ................................................ 10-036462

(51) Int. Cl.[7] ........................................................ G01B 9/02
(52) U.S. Cl. .......................................... 356/479; 356/497
(58) Field of Search .................................. 356/479, 497; 351/205; 606/4, 10

(56) References Cited

U.S. PATENT DOCUMENTS 5,321,501 * 6/1994 Swanson et al. ..................... 356/479
5,465,147 * 11/1995 Swanson .............................. 356/497
5,892,583 * 4/1999 Li ........................................ 356/497

FOREIGN PATENT DOCUMENTS

| | | |
|---|---|---|
| 762077 | 3/1997 | (EP) . |
| 762079 | 3/1997 | (EP) . |
| 62-63824 | 3/1987 | (JP) . |
| 2-140636 | 5/1990 | (JP) . |
| 2-140640 | 5/1990 | (JP) . |
| 4-225134 | 8/1992 | (JP) . |
| 7-265316 | 10/1995 | (JP) . |
| 8-226856 | 9/1996 | (JP) . |
| 8-252256 | 10/1996 | (JP) . |
| 9-108226 | 4/1997 | (JP) . |
| 10-90117 | 4/1998 | (JP) . |

OTHER PUBLICATIONS

"Optical Coherence Tomography," *Science*, vol. 254, Nov. 22, 1991, pp. 1178–1181, Huang, et al.

* cited by examiner

*Primary Examiner*—Samuel A. Turner
(74) *Attorney, Agent, or Firm*—Kilpatrick Stockton LLP

(57) ABSTRACT

An optical measuring instrument which enables measurement of necessary data in a short period of time and uses a light with a short coherence length. In this instrument, such a light emitted from a light source is divided into a measurement light and a plurality of reference lights. The plurality of reference lights are processed by different frequency modulations, and then multiplexed with a light reflected from a measurement object irradiated by the measurement light. On the basis of an output of a photoelectric converter for detecting the level of the multiplexed light and the frequency of each reference light, optical characteristic data related to a plurality of measurement points are calculated.

21 Claims, 15 Drawing Sheets

OPTICAL COHERENCE TOMOGRAPHY HAVE PLURAL REFERENCE BEAMS OF DIFFERING MODULATIONS

TECHNICAL FIELD

The present invention relates to an optical measuring instrument for measuring an optical characteristic of a sample, and specifically, to an optical measuring instrument used for inspecting an internal structure of a sample of a living body.

BACKGROUND ART

A variety of technologies capable of nondestructively inspecting an internal structure of a sample have been developed over the recent years and utilized in many fields. One known technology of such a type is an optical coherence tomography (OCT) for obtaining a coaxial tomographic image of the sample with the use of a light beam having a short coherence length.

The OCT will hereinafter be outlined. The OCT involves the use of an optical measuring instrument including a light source for emitting a light beam having a short coherence length (on the order of several tens of $\mu$m), an interferometer constructed of an optical multiplexer/demultiplexer, a movable reflection mirror and a scan system, and an analyzing system.

The short coherence length light emitted by the light source provided in the optical measuring instrument is guided to the optical multiplexer/demultiplexer constituting the interferometer, and separated into a beam of measurement light and a beam of reference light. The measurement light is guided to a sample (e.g., an eye) via the scan system for changing a position for guiding the measurement light to the sample, then reflected within the sample, and travel back to the optical multiplexer/demultiplexer via the scan system. On the other hand, the reference light is reflected by the reflection mirror moving back and forth in a distance range corresponding to a measuring range of the sample in a direction of the optical axis of the reference light, thereafter travels back to the optical multiplexer/demultiplexer, and is multiplexed by the optical multiplexer/demultiplexer with the reflected light from the sample. Incidentally, for facilitating a process in the analyzing system, the reflection mirror generally takes such a motion pattern that there exists a time zone in which the reflection mirror moves at a fixed velocity such that it returns to a starting point at a high velocity after moving at a fixed velocity from the starting point to an ending point of the distance range.

The analyzing system executes a process of obtaining a corresponding relationship between a position of the reflection mirror and a degree to which the light multiplexed by the optical multiplexer/demultiplexer is modulated (i.e., a process of obtaining optical characteristic data about several positions, having different depths, of a portion to which the measurement light is introduced), and stores a result of this process. When obtaining a sectional image perpendicular to the optical axis of the measurement light, the measurement light beams are introduced to the respective positions required to be measured by the scan system, and the analyzing system calculates and stores the optical characteristic data about the respective positions. Then, the analyzing system obtains plural pieces of optical characteristic data, and, based on these pieces of optical characteristic data, creates and displays the sectional image.

That is, the OCT-oriented optical measuring instrument utilizes the short coherence length light for distinguishing the light beam reflected in a specified position among a multiplicity of light beams simultaneously incident upon the optical multiplexer/demultiplexer and reflected in a multiplicity of positions having different depths within the sample. More specifically, as a result of being reflected in the positions having the different depths, the light beams which have reached simultaneously the optical multiplexer/demultiplexer are defined as short coherence length light beams with different demultiplexing times at which the optical multiplexer/demultiplexer has demultiplexed the measurement light as a basis. Therefore, what interferes with the reference light coming from the reflection mirror among those light beams is only the reflected light of the measurement light demultiplexed by the optical multiplexer/demultiplexer at the same time as that of the reference light, i.e., the light reflected in such a position that a length of an optical path of the measurement light is equal to a length of an optical path of the reference light. Then, a wavelength of the reference light is shifted due to the motion of the reference mirror, and hence the light multiplexed by the optical multiplexer/demultiplexer is the light modulated corresponding to a magnitude of the measurement light component representing an optical characteristic of the depth determined by the length (correlated to the position of the reference mirror) of the optical path of the reference light at that point of time within the sample. Therefore, the analyzing system analyzes a degree of modulating an intensity of the light multiplexed by the optical multiplexer/demultiplexer in connection with a position of the reflection mirror, thereby making it feasible to obtain the optical characteristic at the depth of the portion to which the measurement light is introduced. According to the OCT, the measurement based on the principle described above is repeated at respective points in the sample, thus obtaining two- and three-dimensional images of the sample.

Note that the OCT technology is exemplified in the form of a literature on pp.1178–1181 of "Optical Coherence Tomography", written by D. Huang et al., Science, 1991, 254.

As obvious from the description given above, a spatial resolution of the OCT-oriented optical measuring instrument (which is hereinafter simply referred to as the optical measuring instrument), is basically determined by a coherence length of the light used for the measurement. Therefore, the measurement can be carried out with a higher spatial resolution than by other measuring technologies such as an ultrasonic measuring technology (a spatial resolution is on the order of 150 $\mu$m when measuring at 10 MHz conceived as a general measurement condition) and a laser scan microscope technology (a spatial resolution is on the order to 200 $\mu$m when measuring an eyeground).

The prior art optical measuring instrument is, however, a single channel type instrument capable of measuring only one point existing on the optical axis of the measurement light in the measurement at a certain time, and therefore requires much time for measuring a plurality of points having different depths. It must be a problem in terms of a cost performance that a long time is required for the measurement. Further, if difficult to maintain a measurement object sample in the same position for a long period of time as in the case of a living body sample, a problem in terms of a measuring accuracy might be induced. For example, when measuring an eyeball, it might happen that a relative positional relationship between the optical measuring instrument and the measurement object sample fluctuates due to a motion of the head of a subject and to a fixation micronystagmus. In the prior art optical measuring instrument, a comparatively long time is needed for finishing the measurement in a target range, and therefore, in the meantime, a fluctuation is seen in this positional relationship, with the result that optical characteristic data on positions other than the target position are frequently measured.

DISCLOSURE OF THE INVENTION

It is an object of the present invention to provide an optical measuring instrument capable of making a measurement to obtain necessary data in a shorter period of time.

To accomplish the above object, according to a first aspect of the present invention, an optical measuring instrument comprises optical multiplexing means for multiplexing incident light, light emitting means for emitting the light having a short coherence length, optical demultiplexing means for demultiplexing the light emitted by the light emitting means into a measurement light beam and first through N-th reference light beams, reference light introducing means for modulating the first to N-th reference light beams demultiplexed by the optical demultiplexing means in patterns different from each other and introducing the thus modulated first through N-th reference light beams to the optical multiplexing means, measurement light introducing means for introducing the measurement light demultiplexed by the optical demultiplexing means to a measurement object sample and introducing the measurement light reflected and scattered within by the measurement object sample to the optical multiplexing means, photoelectric converting means for outputting an electric signal assuming a level corresponding to an intensity of the light multiplexed by the optical multiplexing means, and calculating means for calculating optical characteristic data about first through N-th measuring points existing in positions corresponding to lengths of optical paths extending from the optical demultiplexing means of the first through N-th reference light beams to the optical multiplexing means at that point of time within the measurement object sample from the electric signals outputted by the photoelectric converting means by use of a quantity of the modulation effected on the first through N-th reference light beams by the reference light introducing means.

In the thus constructed optical measuring instrument according to the first aspect, the modulation with the pattern different from that of the multiplexed light to which other reference light beams are related is effected upon the multiplexed light of the reflected light beams from points, existing in the positions corresponding to the lengths of the optical paths extending from the optical demultiplexing means of the i-th (i=1 to N) reference light beams to the optical multiplexing means, of the measurement object sample, and of the I-th reference light beam. Namely, the light outputted from the optical multiplexing means contains in a distinguishable form the information indicating the optical characteristics of N-pieces of measuring points each having a different depth. Therefore, the calculating means is capable of calculating the optical characteristic data about the N-pieces of measuring points at once on the basis of a time variation pattern of the electric signals outputted by the photoelectric converting means.

Thus, the present optical measuring instrument is capable of simultaneously measuring the optical characteristic data about the plurality of measuring points and therefore completing the measurement in a shorter period of time than by the prior art optical measuring instrument. Further, since the plurality of measuring points can be simultaneously measured to obtain the optical characteristic data thereabout, a depthwise relative positional accuracy of each of these measuring points is extremely high.

When actualizing the first optical measuring instrument, the reference light introducing means taking a variety of configurations may be adopted.

For instance, there may be used the reference light introducing means including first through N-th reflectors provided in positions upon which the first through N-th reference light beams produced through demultiplexing by the optical demultiplexing means is incident, introducing means for introducing to the optical multiplexing means the first through N-th reference light beams reflected by the first through N-th reflectors, and reflector position control means for modulating the first through N-th reference light beams in patterns different from each other by controlling positions of the first through N-th reflectors.

Furthermore, in the case of using the thus constructed reference light introducing means, what is used as the first through N-th reflectors may be reflectors, of which side surfaces receive incidences of the reference light beams, each having a rotary shaft and assuming such configuration that a distance of the side surface upon which the reference light beam is incident from the center of the rotary shaft, changes corresponding to an angle of rotation of the rotary shaft. The reflector position control means involves the use of means for controlling the angle of rotation of the rotary shaft of each reflector.

Moreover, the first through N-th reflectors may also involve the use of reflectors, fixed to the same rotary shaft, of which side surfaces receive incidences of the reference light beams, each assuming such a configuration that a distance of the side surface upon which the reference light beam is incident from the center of the rotary shaft, changes corresponding to the angle of the rotation of the rotary shaft besides at a rate different from rates of the changes in the distance of other reflectors.

Further, when structuring the optical measuring instrument according to the first aspect, there may be used reference light modulating means including the first through N-th reflectors fixed to a fixing member having the rotary shaft so that the distances thereof from the rotary shaft are different from each other, the introducing means for introducing to the optical multiplexing means the first through N-th reference light beams reflected by the first through N-th reflectors, and the reflector position control means for modulating the first through N-th reference light beams in the patterns different from each other by controlling the angle of rotation of the rotary shaft.

When using the thus constructed reference light modulating means, it is desirable that cylindrical mirrors be used as the first through N-th reflectors, or that, with the first through N-th reflectors being rotatably fitted to a fixing member, the reflector position control means involve the use of means for controlling a position of the fixing member and controlling angles of the first through N-th reflectors to the fixing member so that reflecting surfaces of the first through N-th reflectors are directed in a direction corresponding to a tilt of the fixing member.

Further, there may be used the reference light introducing means including first through N-th optical fibers, for introducing to the optical multiplexing means the first through N-th reference light beams produced by demultiplexing by the optical demultiplexing means, these optical fibers being partially wound on first through N-th electrostrictive elements, and electrostrictive element control means for controlling the first through N-th electrostrictive elements so as to modulate the first through N-th reference light beams in the patterns different from each other. The reference light introducing means including an acousto-optic element for modulating the reference light beam may be used.

Moreover, there may be used the reference light introducing means including optical media exhibiting a distribution of refractive indexes, provided on optical paths of the first through N-th reference light beams, and optical medium position control means for modulating the first through N-th reference light beams in the patterns different from each other by changing relative positions of the optical media with respect to the optical paths of the first through N-th reference light beams.

According to a second aspect of the present invention, an optical measuring instrument comprises optical multiplexing means for multiplexing incident light, light emitting means for emitting first through N-th light beams having a short coherence length and wavelengths different from each other, optical demultiplexing means for generating first through N-th reference light beams and first through N-th measurement light beams by demultiplexing the first through N-th light beams emitted by the light emitting means into reference light beams and measurement light beams, reference light introducing means for modulating the first to N-th reference light beams generated by the optical demultiplexing means and introducing these reference light beams to the optical multiplexing means, measurement light introducing means for introducing the first through N-th measurement light beams having undergone the demultiplexing by the optical demultiplexing means to one point of a measurement object sample and introducing to the optical multiplexing means the first through N-th measurement light beams reflected and scattered within by the measurement objet sample, photoelectric converting means for outputting an electric signal assuming a level corresponding to an intensity of the light multiplexed by the optical multiplexing means, and calculating means for calculating optical characteristic data about first through N-th measuring points existing in positions corresponding to lengths of optical paths extending from the optical demultiplexing means of the first through N-th reference light beams to the optical multiplexing means at that point of time within the measurement object sample from the electric signals outputted by the photoelectric converting means by use of patterns of modulation effected on the first through N-th reference light beams by the reference light introducing means and information on wavelength of the first through N-th reference light beams.

Namely, according to the second aspect of the present invention, the means for emitting the first through N-th light beams having the wavelengths different from each other, is adopted as the light emitting means, whereby the multiplexed light to which the respective reference light beams are related are modulated in the patterns different from each other without using the means having an intricate construction as the reference light introducing means.

The optical measuring instrument according to the second aspect is also capable of simultaneously measuring the plurality of measuring points to obtain the optical characteristic data, and hence, as in the case of the optical measuring instrument according to the first aspect, it is possible to obtain the data exhibiting an extremely high depthwise relative positional accuracy.

On the occasion of constructing the optical measuring instruments according to the first and second aspects, the reference light introducing means may involve the use of means for maintaining, when the calculating means obtains the electric signals for calculating the optical characteristic data, a state where a variation width of each of the optical paths of the first through N-th reference light beams which extend from the optical demultiplexing means of the first through N-th reference light beams to the optical multiplexing means, becomes approximately a coherent light length, or under, of the light emitted by the light emitting means.

If the variation width of the length of the optical path of the reference light is thus limited, the optical measuring instrument may further comprise reference light optical path length changing means for changing the lengths of the optical paths of the first through N-th reference light beams. Further, in the case of limiting the variation width, it is desirable that there be adopted reference light introducing means for making the first through N-th reference light beams subjected to a frequency modulation in a configuration of sine wave with an amplitude being set so that a DC component contained in the electric signal outputted by the photoelectric converting means becomes "0".

Moreover, the optical measuring instruments according to the first and second aspects may further comprise detecting means for detecting a modulation pattern given to each of the reference light beams by the reference light introducing means, and the calculating means may involve the use of means for calculating the optical characteristic data about the first through N-th measuring points by use of the electric signals outputted by the photoelectric converting means and a result of the detection by the detecting means.

The optical measuring instrument according to the first or second aspect may also comprise measurement light introducing position changing means for changing a position to which the measurement light introducing means introduce the measurement light, and storing means for storing introducing position information defined as information indicating the introducing position in such a form that a use order is recognizable, and the calculating means may involve the use of means for calculating the optical characteristic data about the respective measuring points on which the introducing position information stored in the storing means by controlling the measurement light introducing position changing means on the basis of the position information stored in the storing means.

In the optical measuring instrument, the storing means may involve the use of means for storing the introducing position information and measuring time information in such a form that the use order is recognizable. The calculating means may involve the use of means for calculating the optical characteristic data by using the electric signals outputted by the photoelectric converting means for a time corresponding to the measuring time information corresponding to each of the measuring points with respect to the measuring points on which the introducing position information stored in the storing means.

According to a third aspect of the present invention, an optical measuring instrument comprises optical multiplexing means for multiplexing incident light, light emitting means for emitting the light having a short coherence length, optical demultiplexing means for demultiplexing the light emitted by the light emitting means into a measurement light beam and reference light beams, reference light modulating means for generating modulation reference light beams, by utilizing multi-reflections of the reference light, containing a plurality of light components of which frequencies and optical path lengths to positions of being introduced by the optical multiplexing means are different from each other on the basis of the reference light beams produced through demultiplexing by the optical demultiplexing means, and for introducing the modulation reference light beams to the optical multiplexing means, measurement light introducing means for introducing the measurement light beams produced through demultiplexing by the optical demultiplexing means into the measurement object sample and introducing the measurement light beams reflected and scattered within by the measurement object sample to the optical multiplexing means, photoelectric converting means for outputting an electric signal assuming a level corresponding to an intensity of the light multiplexed by the optical multiplexing means, and calculating means for calculating optical characteristic data about a plurality of measuring points within the measurement object sample from the electric signals outputted by the photoelectric converting means on the basis of frequencies of a plurality of optical components contained in the modulation reference light beams and a length of the optical path extending from the light emitting means to the optical multiplexing means.

That is, the optical measuring instrument according to the third aspect of the present invention includes the reference light modulating means for generating the modulation reference light beams by utilizing the multi-reflections of the reference light beams as the means for generating the light beams (which are the modulation reference light beams containing the plurality of light components of which the frequencies and the optical path lengths to the positions of being introduced to the optical multiplexing means are different from each other) needed for making the light outputted from the optical multiplexing means contain in a distinguishable form the information indicating the optical characteristics about the plurality of measuring points having the depths different from each other.

This reference light modulating means can be actualized with a small number of optical elements, and therefore the optical measuring instrument according to the third aspect can be manufactured in a more compact configuration at a lower cost than in the optical measuring instruments according to other aspects of the invention.

It is to be noted that the reference light modulating means may include a half-mirror upon which the reference light is incident, a total reflection mirror for reflecting the light penetrating the half-mirror to make this beam of light travel back to the half-mirror, moving means for moving the half-mirror or the total reflection mirror in a direction of its normal line, and modulation reference light introducing means for introducing the light returned by the total reflection mirror and penetrating the half-mirror as modulation reference light to the optical multiplexing means.

In this reference light modulating means, some proportion of the reference light beams are reflected by the half-mirror onto the same optical axis as that of the incident light. Some other beams of the reference light pass through the half-mirror, and are reflected by the total reflection mirror. The same reference light beams again travel through the half-mirror and exit onto the same optical axis as that of the reference light. Further, some other beams of the reference light pass through the half-mirror, and are reflected respectively by the total reflection mirror, the half-mirror and the total reflection mirror. Then, the same light beams travel through the half-mirror and exit onto the same optical axis as that of the reference light. Moreover, some other beams of the reference light are reflected n-times (n=3, 4, . . . ) by the total reflection mirror and thereafter exit onto the same optical axis as that of the reference light.

Then, when the total reflection mirror (or the half-mirror) is moved by the moving means, the reference light undergoes a Doppler shift upon a reflection by the total reflection mirror (or the half-mirror), and hence the light introduced as the modulation reference light to the optical multiplexing means contains a plurality of light components of which frequencies are shifted from the frequency of the reference light with a quantity corresponding to the number of reflections by the total reflection mirror (or the half-mirror), and of which optical path lengths are different from each other. Namely, the light (the modulation reference light) supplied to the optical multiplexing means from the present reference light modulating means is capable of making the light outputted from the optical multiplexing means contain in the distinguishable form the information indicating the optical characteristics of the plurality of measuring points having the different depths (the above modulation reference light is capable of making the optical measuring instrument function).

Further, the reference light modulating means may include a half-mirror upon which the reference light is incident, a first total reflection mirror for reflecting the light penetrating the half-mirror to make this beam of light travel back to the half-mirror, a second total reflection mirror for returning to the half-mirror the reflected light, by the half-mirror, of the light coming from the first total reflection mirror, moving means for moving the first total reflection mirror in a direction of its normal line, and modulation reference light introducing means for introducing the light returned to the half-mirror by the first total reflection mirror and penetrating the half-mirror as modulation reference light to the optical multiplexing means.

In this reference modulating means, some beams of the reference light are reflected by the half-mirror in a direction different from the optical axis of the reference light. As a result, the light (the modulation reference light) exiting from the optical modulating means onto the same optical axis as that of the reference light does not contain the light which is not reflected by the first total reflection mirror.

Further, some other beams of the reference light pass through the half-mirror and are reflected by the first total reflection mirror. The same reference light beams again travel through the half-mirror and exit onto the same optical axis as that of the reference light. Further, some other beams of the reference light pass through the half-mirror, and are reflected respectively by the first total reflection mirror, the half-mirror, the second total reflection mirror, the half-mirror and the first total reflection mirror. Thereafter, the same light beams travel through the half-mirror and exit onto the same optical axis as that of the reference light. Moreover, some other beams of the reference light are reflected n-times (n=3, 4, . . . ) by the first total reflection mirror and thereafter exit onto the same optical axis as that of the reference light.

Then, when the first total reflection mirror is moved by the moving means, the reference light undergoes a Doppler shift upon a reflection by the first total reflection mirror, and hence the light introduced as the modulation reference light to the optical multiplexing means contains only a plurality of light components of which frequencies are shifted from the frequency of the reference light with a quantity corresponding to the number of reflections by the first total reflection mirror.

Namely, the light (the modulation reference light) supplied to the optical multiplexing means from this reference light modulating means is capable of making the light outputted from the optical multiplexing means contain in the distinguishable form the information indicating the optical characteristics of the plurality of measuring points having the different depths, as well as being the light which does not contain the light component (having the same frequency as that of the measurement light) having the frequency as that of the incident reference light. Then, the present optical measuring instrument obtains the optical characteristic data by utilizing the interference of the short coherence length light, and it is therefore not required that the light multiplexed by the optical multiplexing means with the measurement light from the measurement object sample should contain the light component having the same frequency as that of the measurement light. When the above light component is not contained therein, it follows that the light supplied to the photoelectric converting means from the optical multiplexing means contains a much larger quantity of the light component used for the calculation of the optical characteristic data. Accordingly, the optical measuring instrument constructed by adopting this reference light modulating means is capable of making the high-accuracy measurement (or lessens the load on the photoelectric converting means or the calculating means in order to perform the measurement at the accuracy required).

Note that the optical measuring instrument according to the third aspect can be actualized by use of the reference light modulating means adopting the moving means for moving not the first total reflection mirror but the second total reflection mirror in the direction of normal line. However, the reference light modulating means adopting this moving means outputs modulation reference light containing the light component having the same frequency as that of the incident reference light (light component having the same frequency as the measurement light). Therefore, when the optical measuring instrument according to the third aspect is realized, it is preferable to employ the reference light modulating means having the moving means for moving the first total reflection mirror.

BEST MODE FOR CARRYING OUT THE INVENTION

Embodiments of the present invention will hereinafter be specifically described with reference to the accompanying drawings.

<First Embodiment>

Figure 1:
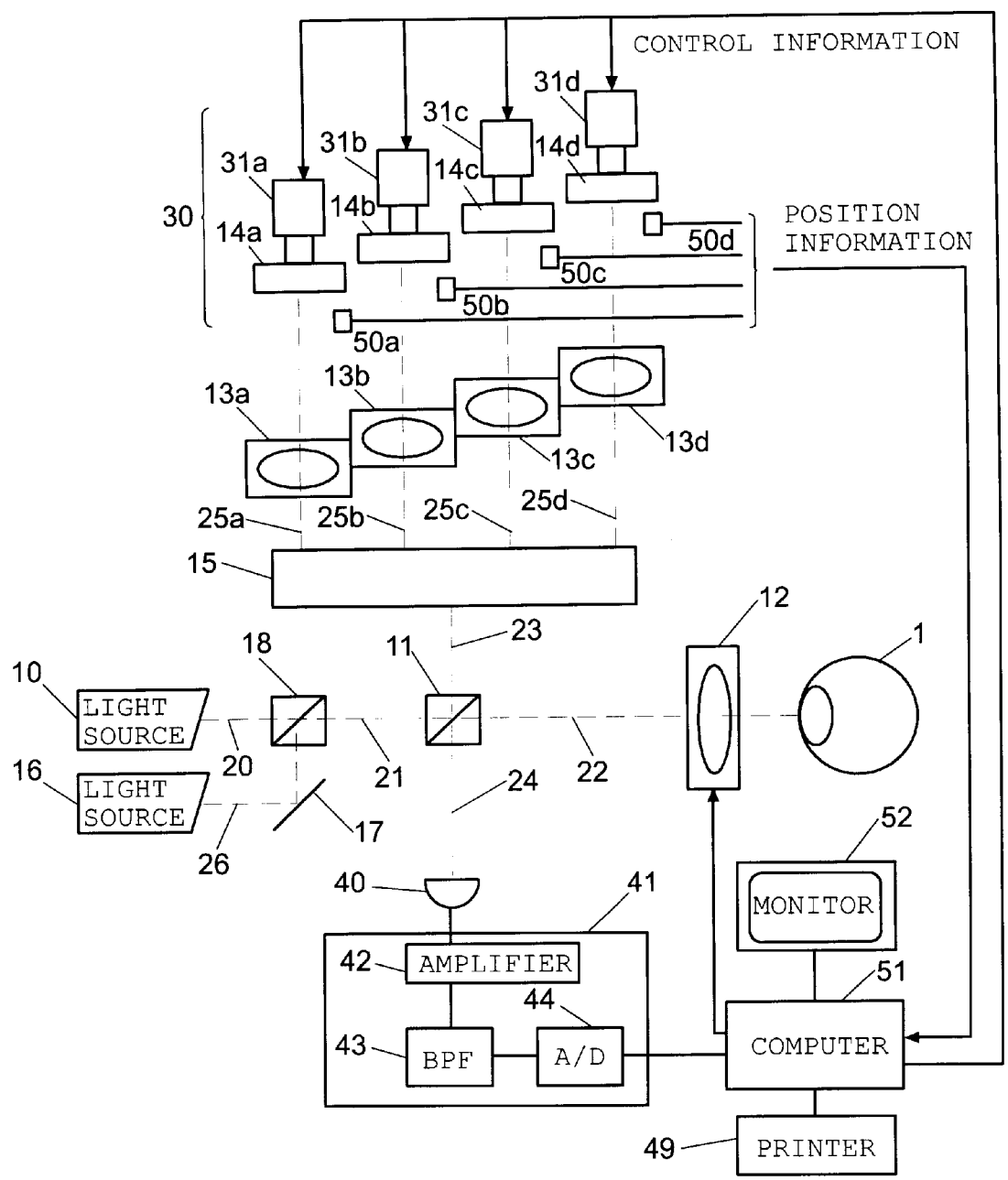
FIG. 1 is a diagram showing a construction of an optical measuring instrument according to a first embodiment of the present invention.

FIG. 1 shows a construction of an optical measuring instrument in a first embodiment. To start with, referring to FIG. 1, there are explained functions of respective components constituting the optical measuring instrument in the first embodiment.

The optical measuring instrument in the first embodiment is an apparatus for a measurement of an eye and, as illustrated therein, includes a light source 10 and a light source 16.

The light source 10 emits beams of light used for the measurement, and is constructed of a super luminescence diode (SLD) for emitting beams of light of which a wavelength is approximately 830 nm and a coherence length is approximately 10 $\mu$m (which is hereinafter referred to as short coherence length light). Note that the reason why the light beams having the wavelength of 830 nm are used for the measurement is that the light beams in a near infrared ray region do not give damages to tissues of the eye to be measured, and exhibit a high penetrance into the tissues. Further, the light source 10 is capable of ON-OFF control by use of digital signals and connected to a computer 51 via an unillustrated signal line.

The light source 16 emits visible light beams and is constructed of a semiconductor laser for emitting light beams having a wavelength of 633 nm.

An optical multiplexer 18 is provided on an optical path 20 along which the light source 10 outputs the short coherence length light beams. Further, a total reflection mirror 17 is provided on an optical path 26 along which the light source 16 outputs the visible light beams. The optical multiplexer 18 is a half-mirror-utilized optical circuit which makes the light beams incident from the side of the optical path 20 travel straight directly (toward an optical path 21), and guides the light beams incident from downward in FIG. 1 toward the optical path 21. The light source 16 and the total reflection mirror 17 are disposed with respect to the optical multiplexer 18 so that the light beams coming from the light source 16 are guided onto the optical path 21.

To be more specific, the light source 16, the total reflection mirror 17 and the optical multiplexer 18 are defined as elements for guiding the visible light beams (which are so-called aiming beams) onto the same optical path as that of the short coherence length light beams. The light source 16 is driven when confirming that an introducing position of the measurement sample is irradiated with the short coherence length light beam. Accordingly, if the light beam in the visible light region is used as the short coherence length light beam (if the object for measurement may be irradiated with such a light beam), the optical measuring instrument can be constructed without providing those elements. Further, in the case of using a CCD camera for making visible the short coherence length light beams reflected and scattered within the measurement object sample and making an observation, the optical measuring instrument can be constructed without providing those elements.

An optical multiplexer/demultiplexer 11 is provided on the optical path 21. The optical multiplexer/demultiplexer 11 is also an optical circuit utilizing the half-mirror. The optical multiplexer/demultiplexer 11 demultiplexes the short coherence length light beams incident from the side of the optical path 21 and deflects the light beams onto an optical path 22 and an optical path 23. The optical multiplexer/demultiplexer 11 also couples (multiplexes) the light beams incident from the sides of the optical paths 22, 23 and converges the light beams onto an optical path 24. Hereinafter, among the short coherence length light beams demultiplexed by the optical multiplexer/demultiplexer 11, the light beams traveling onto the optical path 22 are termed measurement light beams, the light beams traveling onto the optical path 23 are referred to as reference light beams, and the light beams traveling on to the optical path 24 are called interference light beams.

A scan optical system 12 is provided on the optical path 22. The scan optical system 12 incorporates a mechanism for shifting a target position (a measuring position) of the measurement light beams. The scan optical system 12, of which an operation can be controlled by an outside device, is controlled by signals transmitted from a computer 51.

An optical multiplexer/demultiplexer 15, lens systems 13a–13d and a reference light modulating unit 30 are provided on the optical path 23. The reference light modulating unit 30 has reflectors 14a–14d, a reflector driving mechanisms 31a–31d, and position sensors 50a–50d.

The optical multiplexer/demultiplexer 15 is an optical circuit for demultiplexing the reference light incident via the optical path 23 into four beams of reference light which are made to travel on optical paths 25a–25d, and for multiplexing the light beams from the optical paths 25a–25d and converging these light beams onto the optical path 23. The lens systems 13a–13d and the reflectors 14a–14d are disposed in the optical measuring instrument in such a form that the demultiplexed reference light beams exiting onto optical paths 25x (x=a–d) are reflected by the reflector 14x via the lens system 13x and again incident upon the optical multiplexer/demultiplexer 15 via the lens system 13x, and besides, when reflector driving mechanisms 31a–31d which will be explained later on, do not function, lengths of the optical paths of the reference light beams to which the reflectors 14a–14d are related are different from each other.

The reflector driving mechanisms 31a–31d control positions of the reflectors 14a–14d classified as total reflection mirrors in accordance with drive profile specifying data, and are constructed of piezo elements and driving circuits thereof. The computer 51 supplies the reflector driving mechanisms 31a–31d in advance of actual operation with the drive profile specifying data by which the reflectors 14a–14d make motions at velocities different from each other. Then, the driving circuits in the reflector driving mechanisms 31, when instructed by the computer to start the operation, start the control of the piezo elements in accordance with the already given drive profile specifying data.

The position sensors 50a–50d output digital data (position data) indicating displacements from fiducial positions (when the reflector driving mechanisms 31 do not operate) of the reflectors 14a–14d, and as shown in FIG. 1, the position data outputted by the position sensors 50 are supplied to the computer 51.

A photoelectric converter 40 for outputting a current signal assuming a level corresponding to an intensity of the incident light, is provided on the side of the optical path 24. A signal processing circuit 41 constructed of an amplifier 42, a BPF (Band-Pass Filter) 43 and an A/D converter 44 is provided posterior to the photoelectric converter 40. The A/D converter 44 is connected to the computer 51.

The photoelectric converter 40 is a circuit composed of an avalanche photo diode and a driving circuit thereof. The current signal assuming the level corresponding to the intensity of the interference light outputted by the photoelectric converter 40, is converted into a voltage signal and amplified by the amplifier 42 in the signal processing circuit 41. The BPF 43 passes only an AC component, contained in the voltage signal outputted by the amplifier 42, of which a frequency exists in a predetermined region. A pass band of the BPF 43 is set to what corresponds to the drive profile specifying data that may be supplied to the driving control mechanisms 31 (the content of the drive profile specifying data which can be given to the reflector control mechanism 31 is restricted depending on the pass band of the BPF 43). The A/D converter 44, upon receiving an instruction from the computer 51, executes a process of converting an analog voltage signal outputted by the BPF 43 into a digital signal.

The computer 51 is stored with a measurement sequence file creating program, a measurement program, a data processing program, and data on the lengths of the optical paths when the respective reflectors 14 are in the fiducial positions. The measurement sequence file creating program is a program for creating in an interactive manner a measurement sequence file consisting of four items of drive profile specifying data, three-dimensional coordinate data on several points to be measured, and measurement time specifying data of respective measuring points.

The measurement program is started up when performing an actual measurement. The computer 51, when the measurement program is started up, recognizes measurement conditions and procedures based on the data in the measurement sequence file designated by the operator, and measures optical characteristic data about the respective measuring points. Then, the measurement data file stored with measured results is created, and the measurement program thus comes to an end. Further, the data processing program serves to output to a monitor 52 or a printer 49 the data stored in the measurement data file in the form of two- and three-dimensional images or raw data.

A general operation of the optical measuring instrument in the first embodiment will hereinafter be described.

The person (operator) who performs the measurement by use of the present optical measuring instrument creates several (at least one) measurement sequence files containing four items of drive profile specifying data and plural pieces (at least one piece) of measurement condition data by running the measurement sequence file creating program in advance of an actual measurement, and stores the files in the computer 51.

The drive profile specifying data consists in principle of a category specifying data for showing a category of the drive profile, cycle data for specifying a cycle, and data for specifying an amplitude. In the optical measuring instrument in this embodiment, data in which a position of the reflector 14 changes in a configuration of sine wave with respect to the time, and data in which the position changes in a configuration of triangular wave and a serrated configuration, are prepared as the category specifying data. Further, standard values are prepared as the cycle data and the amplitude data, and the operator determines the four items of drive profile specifying data (stores the same data in the measurement sequence file) used for the measurement by combining the respective pieces of data. On this occasion, the operator determines the drive profile specifying data so that moving velocities of the reflectors 14 at respective times are always different (so that time variation patterns of the moving velocities of at least two reflectors 14 are not the same). Note that there are prepared in the computer several pieces of standard data which can be used as the drive profile specifying data and of which contents are set so that a fluctuation width of the reference light optical path length by the motion of the reflector 14 is under the coherence length of the short coherence length light. The operator creates the measurement sequence file normally by selecting the data for use among these pieces of standard data.

Further, the operator sets, in the measurement sequence file, a necessary quantity of measurement condition data consisting of X- and Y-coordinates x, y of the measuring point, four Z-coordinates $Z_a$, $Z_b$, $Z_c$, $Z_d$ and measuring time specifying data t. Herein, the Z-coordinates are coordinates set in a depthwise direction of the measuring point, and X- and Y-coordinates are orthogonal coordinates set on the plane perpendicular to the depthwise direction.

Then, the operator, when starting the actual measurement, runs the measurement program. The computer 51 having started the operation based on the measurement program, to begin with, issues an initializing command to the scan optical system 12, thereby setting a state of the scan optical system 12 as a fiducial state. Namely, the computer 51 sets the position (X, Y) at which the measurement light is introduced as a fiducial position $(x_o, y_o)$.

Subsequently, the computer 51 shifts to a standby status for inputting a name of the measurement sequence file from the operator. Then, when the name of the measurement sequence file is inputted, the computer reads the four items of drive profile specifying data stored in the specified measurement sequence file, and element data $x_i$, $y_i$, $z_{ai}$, $z_{bi}$, $z_{ci}$, $z_{di}$, $t_i$ (i=1–Nmax) in each piece of subsequent measurement condition data. Next, the computer 51 notifies the driving circuit in each of the reflector driving mechanisms 31a–31d, of the four items of drive profile specifying data, and stands by till an operation of instructing the start of the measurement is done.

On the other hand, the operator, after running the measurement program, inputs the name of the measurement sequence file used. Then, while turning on the light source 16 and confirming the position to be irradiated with measurement light, the operator adjusts a position of the measurement object sample 1 (which is a subject in the present measuring instrument) and a position of the optical measuring instrument, whereby the measurement object sample 1 and the optical measuring instrument take a predetermined relative positional relationship. Then, upon finishing the adjustment of the positional relationship, the operator switches OFF the light source 16 and instructs the computer 51 to start the measurement.

Figure 2:
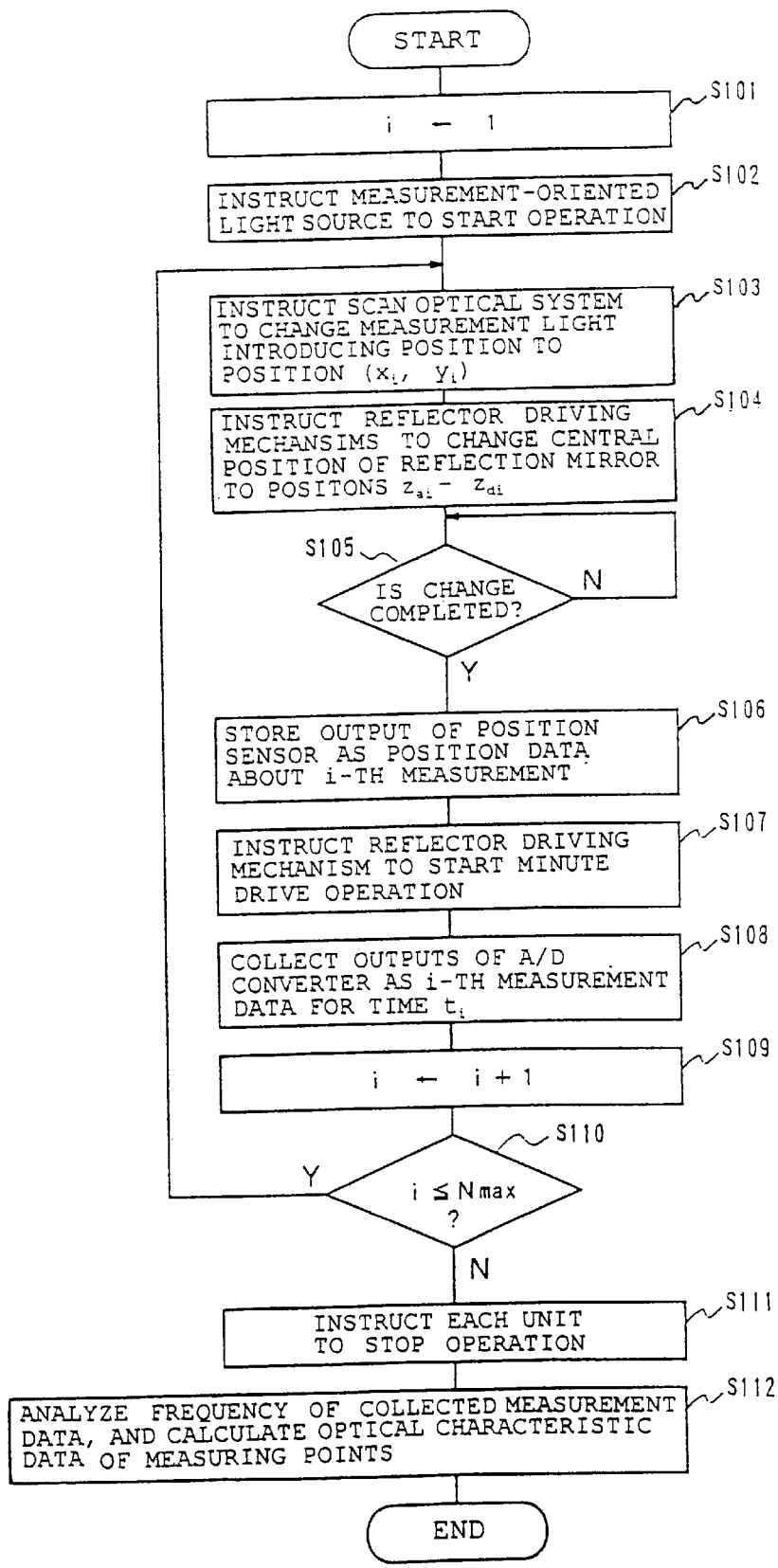
FIG. 2 is a flowchart showing an operating procedure of a computer incorporated into the optical measuring instrument according to the first embodiment.

The computer 51 instructed to start the measurement operates in accordance with a flowchart shown in FIG. 2.

To be specific, the computer 51 at first sets "1" in a variable i (step S101), and instructs the light source 10 (for the measurement) to start the operation (an emission of the short coherence length light beams) (step S102). Further, the computer 51 displays a frame of graph for illustrating the measured results on the monitor 52.

Subsequently, the computer 51 instructs the scan optical system 12 to change the measurement light introducing position to a position $(x_i, y_i)$ (step S103). Further, the computer 51 instructs the reflector driving mechanisms 31a–31d to shift central positions of the reflectors 14a–14d to positions $z_{ai}$–$z_{di}$ (step S104).

Incidentally, as already explained, in the present optical measuring instrument, the reference light optical path length when each reflector is located in the fiducial position is different. The computer 51 therefore instructs the respective reflector driving mechanisms 31 to make the sifts to the positions $z_{ai}$–$z_{di}$ taking into consideration the difference between the reference light optical path lengths in step S104. More specifically, the reflector driving mechanisms are supplied with control information containing data in which the positions $z_{ai}$–$z_{di}$ are converted into data corresponding to lengths from the fiducial position. Further, though not shown in the flowchart, if there is no necessity for changing the position $(x_i, y_i)$, i.e., when $x_i=x_{i-1}$ and $y_i=y_{i-1}$, the computer 51 finishes step S103 (proceeds to step S104) without giving the instruction to the scan optical system 12. Similarly, if there is no necessity for changing the position $z_{xi}$ (x=a–d) (when $z_{xi}=z_{xi-1}$), the computer 51 finishes step S104 without giving the instruction to the reflector driving mechanism 31x.

After finishing step S104, the computer 51 stands by till information showing a completion of the positional change is inputted from the device having been given the instruction (step S105) (if there is no device having been given the instruction, step S105 comes to an end without waiting for the input of the information). Then, when receiving the notifications from all the devices having been given the instruction (step S105; Y), the computer 51 obtains the position data from the position sensors 50a–50d as data on an i-th measurement, and stores the same data (step S106). Note that this process is executed for precisely recognizing the position of each reflector 14, and, if the reflector driving mechanism 31 is capable of moving the reflector 14 to a position as the computer 51 instructs, step S106 can be omitted.

Subsequently, the computer 51 instructs the driving circuits in the reflector driving mechanisms 31a–31d to start a minute driving operation (which is a drive control operation based on the drive profile specifying data) (step S107). Then, the computer 51 starts a process of cyclically obtaining the data from the A/D converter 44, and stores each piece of obtained data as i-th measurement data (step S108). Furthermore, in this step, the computer 51 plots the measurement data in the above-mentioned graphic frame on the monitor 52.

Then, the computer 51, after executing such a process for a time ti, instructs the reflector driving mechanisms 31a–31d to halt the minute driving operation, and finishes step S108.

After the end of step S108, the computer increments a content of the variable i by "1" (step S109), and, if i≧Nmax (step S110; Y), re-executes the processes from step S103 in order to make the next measurement. Whereas if i>Nmax, (step S110; N), the computer 51 instructs the measurement-oriented light source 10 etc to stop the operation (step S111). Then, the computer 51 analyzkes a frequency of each piece of measurement data obtained in step S108 in consideration for the contents of the drive profile specifying data, and calculates and stores optical characteristic data about (4×Nmax) measuring points (step S112). Then, the processes shown therein are ended.

For instance, in the case of giving each of the reflector driving mechanisms 31a–31d the drive profile specifying data in which the relationship between the position and the time is expressed in a triangular wave, a time variation component S(t) of the intensity of the interference light incident upon the photoelectric converter 40 is, on the assumption that there are neither an attenuation of the measurement light within the measurement object sample nor a fluctuation in the light intensity of the light source, expressed by the following formula (1):

$$S(t) \propto \sum_{i=1}^{n} R_i(t)\sin(\omega_i t + \phi_i) \quad (1)$$

where Ri(t) is an intensity of the reflected light at a time t from the measuring point at which the position (a depth) is determined by the i-th reference light optical path length, $\omega_i$ is a modulation angular frequency of the i-th modulated interference light, and $\phi_i$ is a phase.

Thus, the light having a time variation component corresponding to a sum of signals with the reflected light intensity $R_i(t)$ at each measuring point being modulated by the angular frequency $\omega_i$ (i=1~n; n=4 in the embodiment), is incident upon the photoelectric converter 40. The reflected light intensity $R_i(t)$ may be conceived as a value $R_i$ independent of the time for a given short period of time, and hence, if magnitudes of components of the modulation angular frequencies $\omega_i$–$\omega_n$ appearing in a power spectrum S($\omega$) of the interference light are separately obtained (if the angular frequencies $\omega_i$–$\omega_n$ take values different from each other), it follows that the information correlated to the reflected light intensity $R_i$ is obtained.

In the present optical measuring instrument, the drive profile specifying data is determined so that the moving velocities of the reflectors 14 at respective times are different, and therefore the angular frequencies $\omega_i$–$\omega_n$ (n=4 in the embodiment) take the values different from each other. Accordingly, the optical characteristic data on the four measuring points are contained in such a form as to be distinguishable in the outputs of the A/D converter 44, and the computer 51 is capable of calculating at step S102 the optical characteristic data of the four measuring points from the i-th measurement data collected in step S108.

Further, when the drive profile specifying data for changing the reflector position in the configuration of sine wave is given to each reflector driving mechanism, it follows that the output of the A/D converter contains such a signal that its power spectrum is expressed by the following formula (2) with respect to each individual reflector (the measuring point). Therefore, in step S112, the computer is programmed to execute a routine for obtaining the magnitudes of components of the angular frequencies $\omega_r$, 2$\omega_r$ and so on at the respective measuring points by FFT etc.

$$P(\omega) \propto \left| \sum_{n=0}^{\infty} J_n(2kL_a) \frac{\sin\{(\omega - n\omega_r)t_M\}}{(\omega - n\omega_r)} \right|^2 \quad (2)$$

Where $J_n$ is an n-th order Bessel function, k is given by 2$\pi$/$\lambda$, La is an amplitude of an oscillating motion (minute oscillation) of a certain reflector, $\omega_r$ is an angular frequency with the minute oscillation, $t_M$ is a measuring time.

Incidentally, if $2kL_a$ is set to an arbitrary value, there increases a component having a coefficient $J_0(2kL_a)$, i.e., a DC component which can not be distinguished from a noise. It is therefore desirable that relative intensities of the signals of other angular frequencies be enhanced by selecting $2kL_a$ when oscillating the reflector in the configuration in sine wave so that $J_0(2kL_a)$ takes "0". For example, as in the case of the optical measuring instrument in the first embodiment, when using the light beam having a wavelength $\lambda$ of 830 nm as the short coherence length light beam, a value of $2kL_a$ with which $J_0(2kL_a)$ becomes "0" is approximately 2.405. It is therefore desirable that each reflector be oscillated at a different cycle so that $L_a$ becomes approximately 158.9 nm (=2.405×$\lambda$/4$\pi$).

As described in details, it is feasible to simultaneously obtain the optical characteristic data of the four measuring points with different depths by use of the optical measuring instrument in the first embodiment. Therefore, the optical measuring instrument in the first embodiment is capable of completing the measurement in shorter period of time than by the prior art optical measuring instrument.

Note that the optical measuring instrument in the first embodiment is constructed by using the reflector driving mechanisms receiving the various items of drive profile specifying data but may also be constructed by use of reflector driving mechanisms capable of executing only specific drive control. Further, in the optical measuring instrument in the first embodiment, the position sensor is used only for detecting the central position of the reflector, however, the computer may also be programmed so that in step S108 an output of the position sensor is periodically taken in, and a process (a so-called synchronous-tuned detection process) using these pieces of data in step S112.

As a matter of course, the optical measuring instrument may be structured so that a circuit for effecting the s synchronous-tuned detection using the output of the position sensor with respect to an output of the photoelectric converter, is provided anterior to the computer, and an output of this circuit is inputted to the computer.

Moreover, in the optical measuring instrument in the first embodiment, not special medium is used as an optical path, but the whole or a part of the optical path may be of course composed of an optical fiber capable of retaining a plane of polarization, such as a single-mode optical fiber and polarization retaining optical fiber.

<Second Embodiment>

An optical measuring instrument in accordance with a second embodiment has a modified structure of the optical measuring instrument in the first embodiment, in which a configuration of the signal processing circuit and a content of the measurement program executed by the computer are different. Further, the optical measuring instrument in the second embodiment has a less number of categories of the drive profile specifying data settable in the measurement sequence file than in the optical measuring instrument in the first embodiment.

The construction and operation of the optical measuring instrument in the second embodiment, excluding the signal processing circuit and the computer, are absolutely the same as those of the optical measuring instrument in the first embodiment, and hence, with an illustration of the whole construction being omitted herein, the optical measuring instrument in the second embodiment will be explained in conjunction with a diagram (FIG. 3) showing a configuration of the signal processing circuit.

Figure 3:
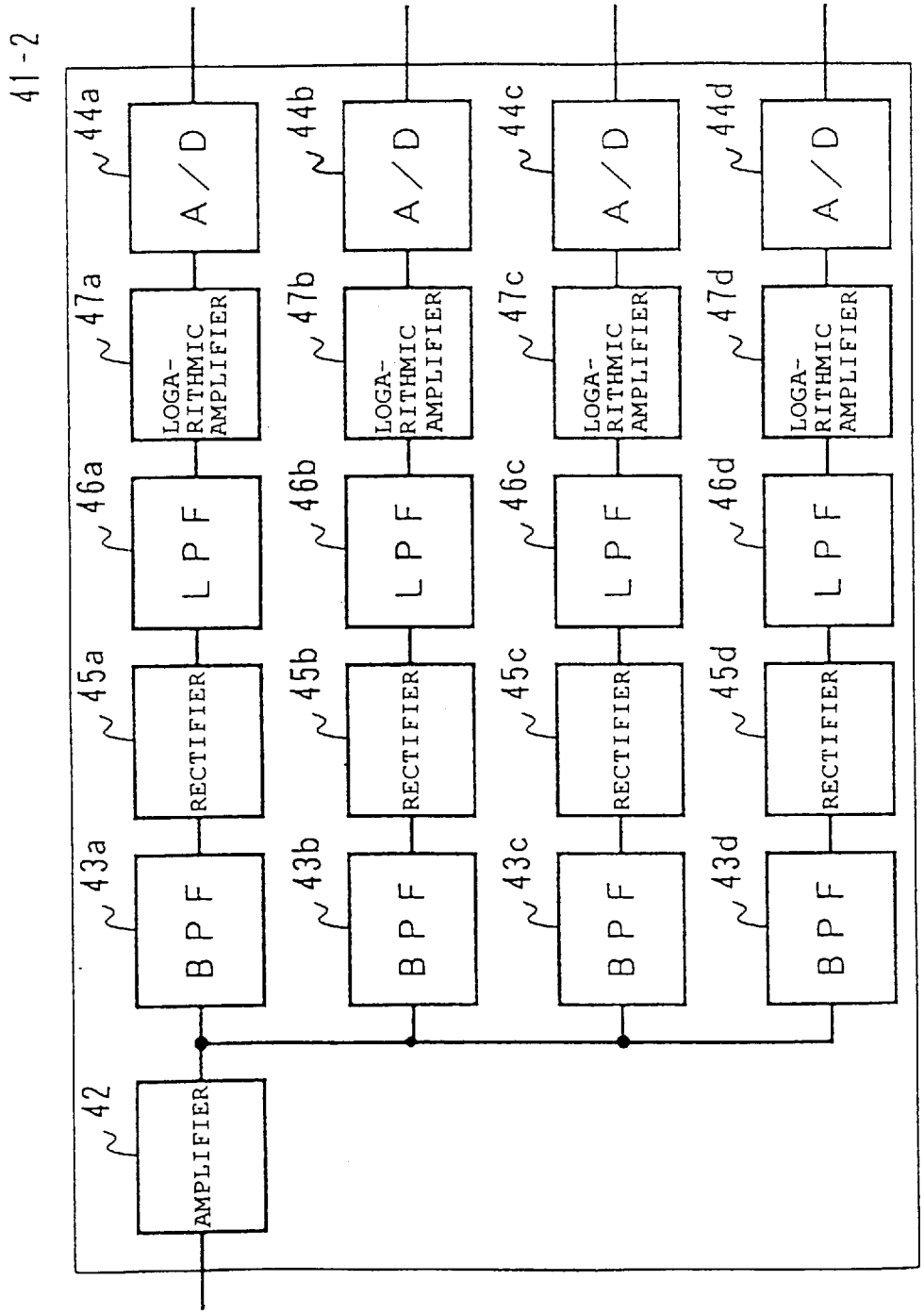
FIG. 3 is a diagram showing a configuration of a signal processing circuit provided in an optical measuring instrument according to a second embodiment of the present invention.

As shown in FIG. 3, a signal processing circuit 41-2 included in the optical measuring instrument in the second embodiment has 4-system circuits provided posterior to an amplifier 42, each circuit being constructed of a BPF 43, a rectifier 45, a LPF (Low-Pass Filter) 46, a logarithmic amplifier 47 and an A/D converter 44. Outputs of the A/D converters 44a–44d are supplied to the unillustrated computer 51. The BPFs 43a–43d respectively filter signals having narrow frequency components with angular frequencies ωa, ωb, ωc, ωd being centered out of outputs of the amplifier 42.

Then, in the optical measuring instrument in the second embodiment, the contents of the drive profile specifying data settable in the measurement sequence file are restricted to one that creates the components of the interference light having the above angular frequencies. More specifically, the category of the drive profile specifying data is restricted to data with which the reflector 14 is driven in the configuration of triangular wave or in the serrated configuration, and a parameter which can be designated is restricted to only the amplitude (the cycle is automatically calculated from the amplitude so that the moving velocity of the reference mirror corresponds to the angular frequencies described above).

Therefore, signals of the interference light components derived from the reference light to which the reflectors 14a–14d are related, are outputted from the BPFs 43a–43d in the signal processing circuit 41-2. The rectifiers 45a–45d rectify AC signals outputted respectively by the BPFs 43a–43d, and LPFs 46a–46d eliminate high-frequency components (noise components) out of the rectified signals. To be specific, the LPFs 46a–46d respectively output DC signals assuming levels correlated to the reflected light intensities at the measuring points different in depths from each other.

The logarithmic amplifiers 47a–47d logarithmically amplify signals transmitted from the LPFs 46a–46d. Namely, the logarithmic amplifiers 49a–49d adjust a dynamic range of the signals from the LPFs 46a–46d. The A/D converters 44a–44d convert analog signals coming from the logarithmic amplifiers 49a–49d into digital signals, and supply these signals to the computer.

Thus, the optical measuring instrument in the second embodiment includes, as a signal processing circuit, the circuit for outputting the data directly correlated to the intensities of the reflected light beams pertaining to the individual measuring points. Therefore, the computer in the present optical measuring instrument is stored with the measurement program for collecting pieces of optical characteristic data without executing the frequency analysis (which is the process corresponding to step S112).

The optical measuring instrument in the second embodiment is also capable of simultaneously obtaining the optical characteristic data of the four measuring points in the different depths and therefore completing the measurement in a shorter period of time than by the prior art optical measuring instrument. Further, an arithmetic throughput of the computer in the optical measuring instrument in the second embodiment is less than in the optical measuring instrument in the first embodiment. Therefore, the instrument of this embodiment operates at a higher speed to that degree.

<Third Embodiment>

An optical measuring instrument in accordance with a third embodiment has a modified structure of the optical measuring instrument in the first embodiment, in which a configuration of a reference light modulating unit and an operating procedure of the computer are different. Therefore, herein, the explanation will concentrate on these points.

Figure 4:
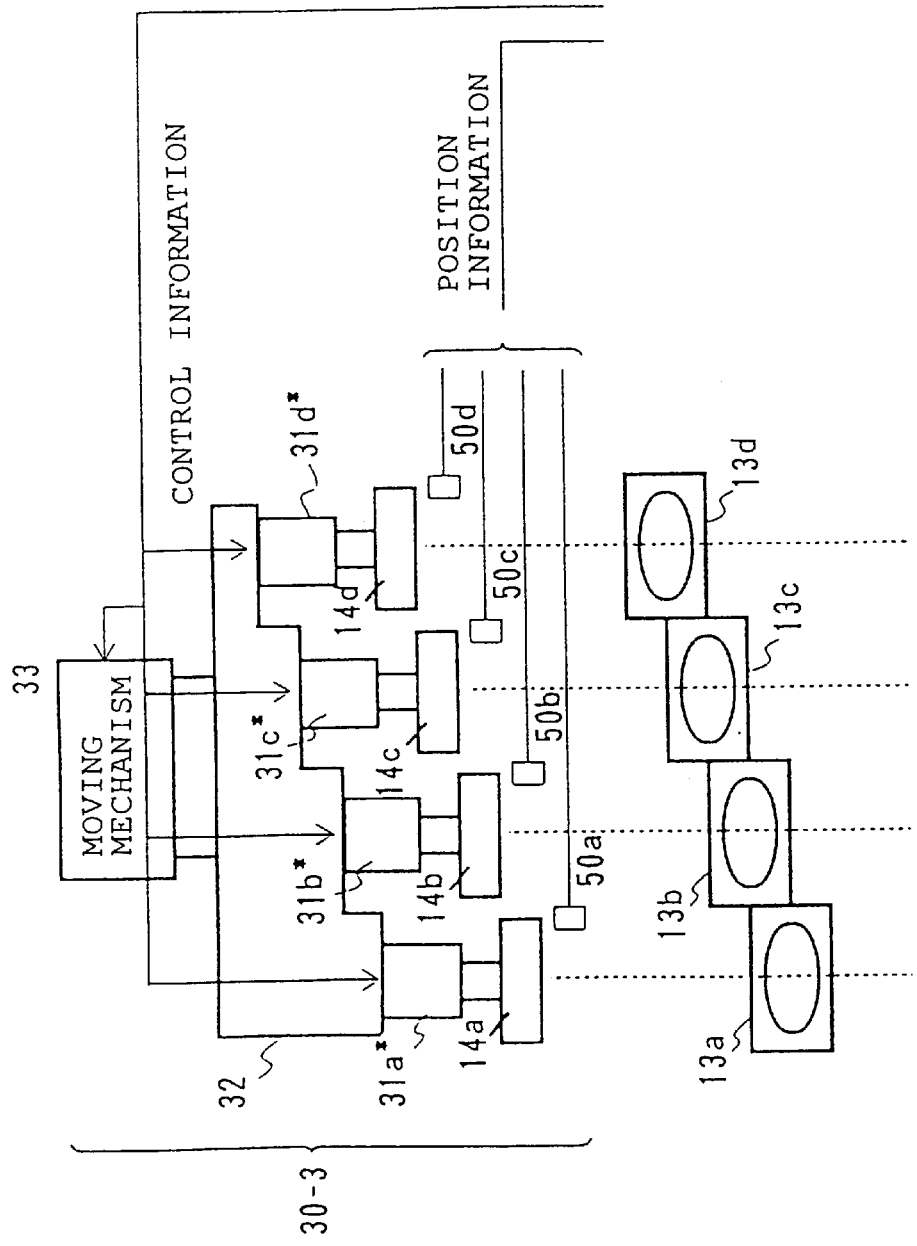
FIG. 4 is a diagram showing a configuration of a reference light modulating mechanism provided in an optical measuring instrument according to a third embodiment of the present invention.

FIG. 4 shows the configuration of the reference light modulating unit provided in the optical measuring instrument in the third embodiment. As illustrated in FIG. 4, the basic configuration of the reference light modulating unit 30-3 in the third embodiment is that a member 32 and a moving mechanism 33 are added to the reference light modulating unit 30 in the first embodiment. The moving mechanism 33 is fixed to one surface of the member 32, while reflector driving mechanisms 31a*–31d* are fixed to the other surface thereof. Note that position sensors 50a–50d fixed to a box body (the moving mechanism 30) of the optical measuring instrument.

The moving mechanism 33 moves the member 32 in up-and-down directions in FIG. 4 and operates upon receiving control information from the computer. The reflector driving mechanisms 31a*–31d* have substantially the same configurations as those of the reflector driving mechanisms 31 in the optical measuring instrument in the first embodiment. The reflector driving mechanisms 31a*–31d*, however, take charge of only the minute driving operations of the reflectors 14a–14d, and the depths of the measuring points are changed by the moving mechanism 33. That is, the reference light modulating mechanism 30-3 is so structured that, when the reflector driving mechanisms 31a*–31d* do not function, Z-coordinates $z_x$ of the measuring points corresponding to lengths of the optical paths of the reference light beams to which the reflectors 14x (x=a–d) are related, can be calculated from Z-coordinates pertaining to other reflectors 14y (y≠x).

Therefore, the measurement sequence file used in the present optical measuring instrument is a file in which are set four pieces of drive profile specifying data and measurement condition data consisting of X- and Y-coordinates x, y and one Z-coordinate z of the measuring points and measuring time specifying data t. Then, the computer in the present optical measuring instrument instructs in a step corresponding to step S104 the moving mechanism 33 to move the reflectors to a position $z_i$. As a result, the reflectors 14a–14d are respectively moved to such positions that the Z-coordinates of the measuring points become $z_i+\Delta z_a$, $z_i+\Delta z_b$, $z_i+\Delta z_c$, $z_i+\Delta z_d$ ($\Delta z_a$, $\Delta z_b$, $\Delta z_c$, $\Delta z_d$ are constants corresponding to a difference between the optical paths of the reference light beams, and are determined by a structure of the reference light modulating mechanism 30-3). Thereafter, the computer executes absolutely the same processes as those by the computer 51 in the optical measuring instrument in the first embodiment.

The thus constructed optical measuring instrument in the third embodiment is, though a degree of freedom of selecting the measuring points for the simultaneous measurements is narrower than in the optical measuring instrument in the first embodiment, still capable of simultaneously measuring the data on the plurality of measuring points. Therefore, the optical measuring instrument in the third embodiment is, if used, capable of completing the measurement of the necessary data in a short period of time. Further, the mechanisms with a narrow movable range of the reflectors can be used as the reflector driving mechanisms $31a^*-31d^*$, and consequently the optical measuring instrument in the third embodiment can be manufactured at a low cost.

<Fourth Embodiment>

An optical measuring instrument in accordance with a fourth embodiment has a modified structure of the optical measuring instrument in the first embodiment, in which a configuration of the reference light modulating mechanism and an operating procedure of the computer are different.

Figure 5:
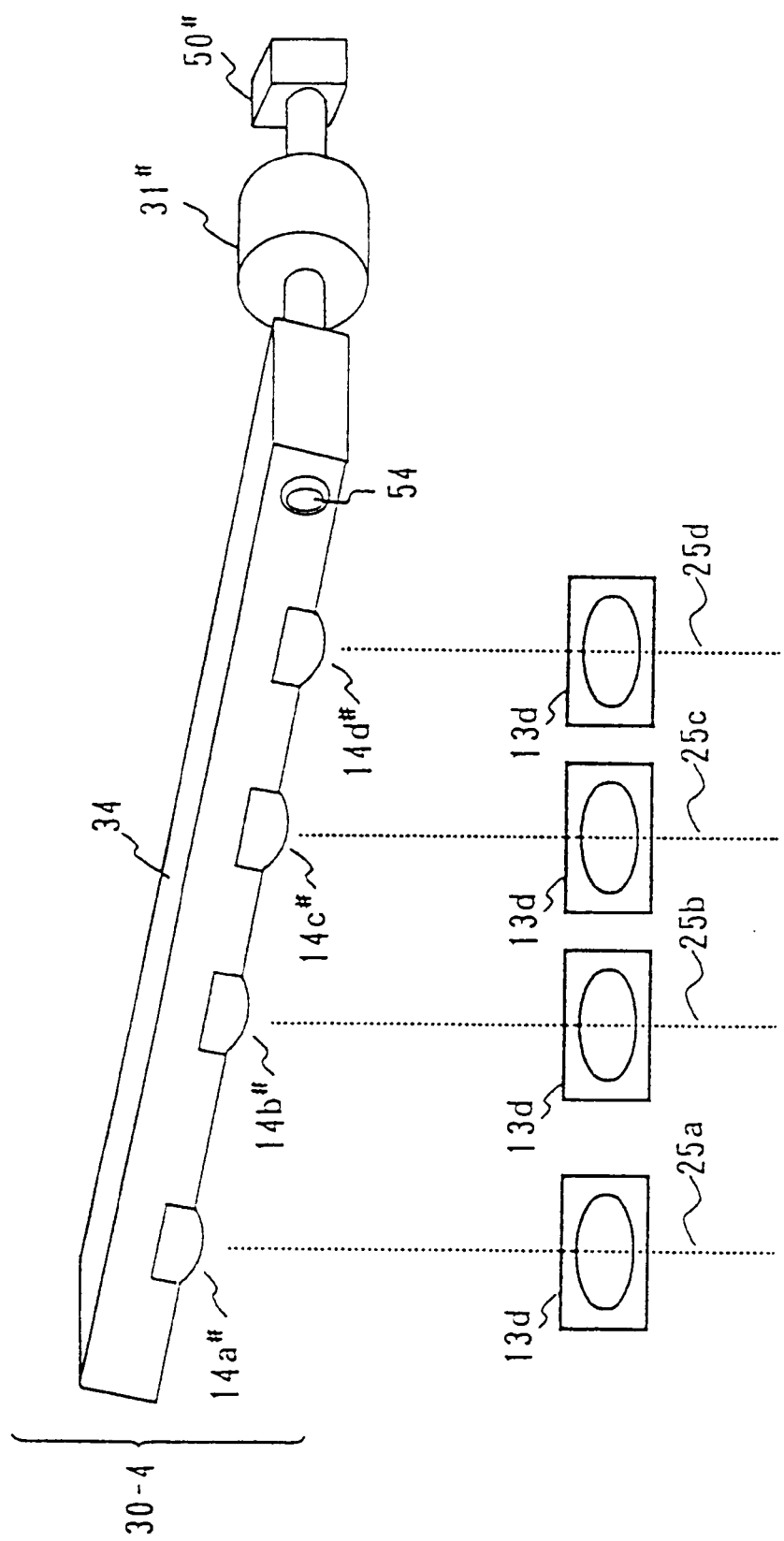
FIG. 5 is a diagram showing a configuration of a reference light modulating mechanism provided in an optical measuring instrument according to a fourth embodiment of the present invention.

FIG. 5 shows the configuration of the reference light modulating mechanism provided in the optical measuring instrument in the fourth embodiment. As illustrated in FIG. 5, the reference light modulating mechanism 30-4 in the fourth embodiment is constructed of reflectors $14a^\#14d^\#$, a fixing member 34 having a rotary shaft 54, a reflector driving mechanism $31^\#$, and a position sensor $50^\#$. The reflectors $14a^\#-14d^\#$ are so-called cylindrical mirrors and respectively attached to the fixing member 34 so that separate reference light beams from corresponding lens systems 13a–13d are incident on the center when the fixing member 34 is in a fiducial position. Furthermore, the reflectors $14a^\#-14d^\#$ have radii of curvature corresponding to distances from (the center of) the rotary shaft 54. Namely, each reflector takes such a form as to reflect the incident light back in the same direction as a direction of the incidence even if the fixing member 34 rotates about the rotary shaft 54.

A reflector driving mechanism $31^\#$ is connected to the rotary shaft 54 of the fixing member 34 and oscillates the fixing member 34 in accordance with a given piece of drive profile specifying data. Namely, in the optical measuring instrument in the fourth embodiment, with the rotation of the rotary shaft 54, a length of the optical path of each reference light beam changes at a velocity corresponding to a ratio of the distance between the rotary shaft 54 and each reflector $14^\#$. A position sensor $50^\#$ is also connected to the rotary shaft 54 and outputs data indicating a rotary angle (a tilt of the fixing member 34) from the fiducial position of the rotary shaft 54.

On the other hand, the unillustrated computer is stored (set) with data about the distances of the reflectors $14a^\#-14d^\#$ from the rotary shaft 54 and data indicating a correspondence between an output of the position sensor $50^\#$ and an actual position (a tilt) of the fixing member 34. Further, the computer, when executing the measurement sequence file creating program, creates a measurement sequence file stored with one piece of drive profile specifying data (consisting of an angle-of-rotation range $\Delta\theta$ and time variation pattern data for specifying a time variation pattern of an angular speed), and with measurement condition data consisting of X- and Y-coordinates x, y and one Z-coordinate z of the measuring point and measuring time specifying data t.

Then, the computer in the present optical measuring instrument, when executing the control based on the measurement program, in a step corresponding to step S104, instructs the reflector driving mechanism $31^\#$ to shift the measuring point relative to the reflector $14d^\#$ to the position $z_i$. As a result, other reflectors $14a^\#-14c^\#$ are moved to such positions that the Z-coordinates of the measuring points become $z_i+\delta z_a(\theta)$, $z_i+\delta z_b(\theta)$, $z_i+\delta z_c(\theta)$ (in the optical measuring instrument in the fourth embodiment, unlike the optical measuring instrument in the third embodiment, the difference between the optical path lengths is a function of the angle θ of the rotary shaft 54). Thereafter, the computer operates the same as the computer 51 in the optical measuring instrument in the first embodiment. That is, the computer instructs the reflector driving mechanism $31^\#$ to start a minute fluctuating operation. The reflector driving mechanism $31^\#$ instructed to start the minute fluctuating operation rotates the rotary shaft 54 within an angle range of ±Δθ/2 with the angle θ being centered at that point of time in accordance with the drive profile specifying data. The computer sequentially obtains pieces of measurement data containing the information on the four measuring points from the signal processing circuit.

The optical measuring instrument in the fourth embodiment is also capable of measuring simultaneously the data about the plurality of measuring points, and therefore, as in the optical measuring instruments in the first through third embodiments, may complete the measurement of the required data in a short period of time. Further, it may suffice for constructing the optical measuring instrument in the fourth embodiment that one single reflector driving mechanism is prepared, and hence the optical measuring instrument in the fourth embodiment can be manufactured at a lower cost than in the optical measuring instruments in the first through third embodiments.

<Fifth Embodiment>

An optical measuring instrument in accordance with a fifth embodiment has, as in the case of the optical measuring instrument in the fourth embodiment, differences in terms of the reference light modulating mechanism and the operating procedure of the computer from those in the optical measuring instrument in the first embodiment.

Figure 6:
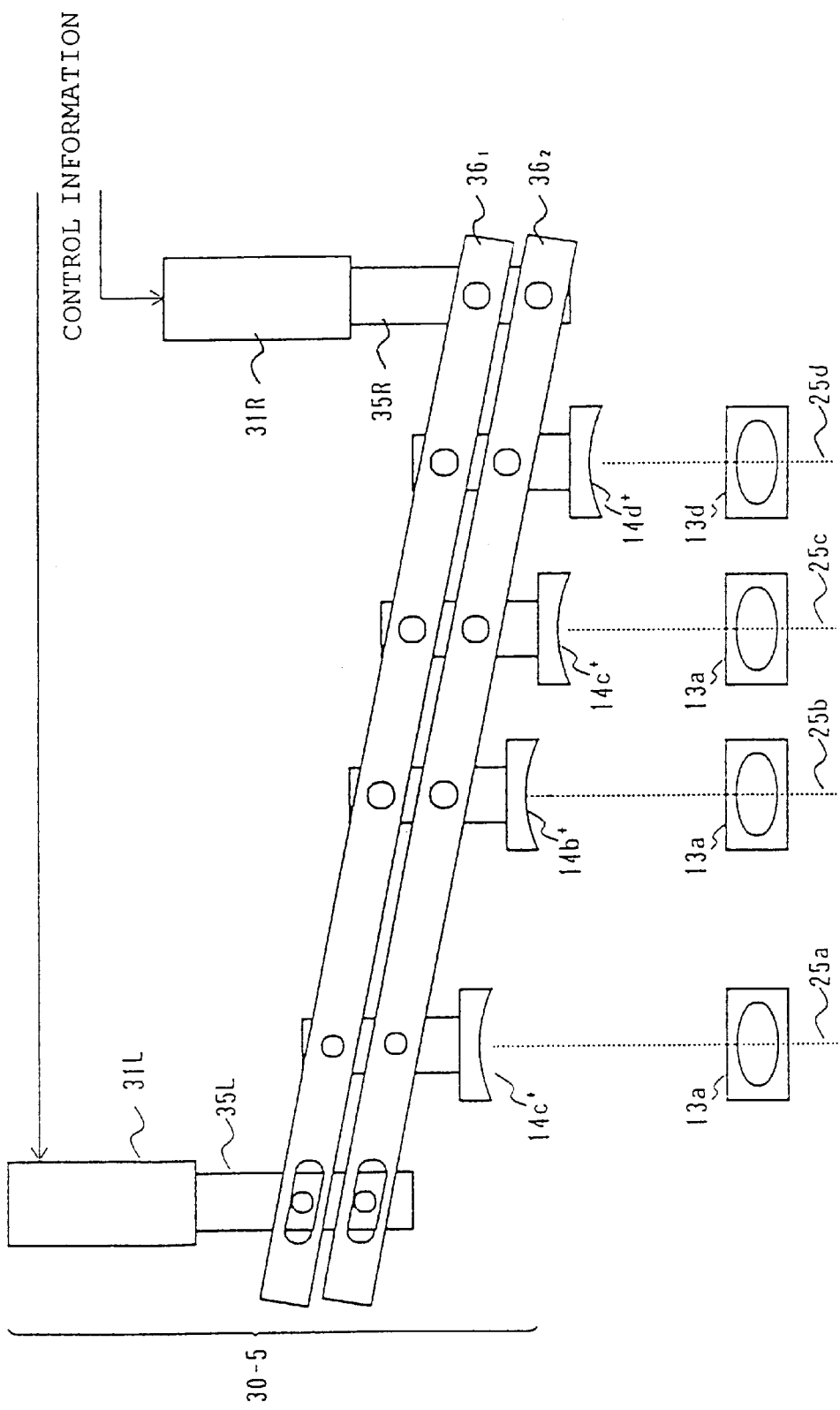
FIG. 6 is a diagram showing a configuration of a reference light modulating mechanism provided in an optical measuring instrument according to a fifth embodiment of the present invention.

FIG. 6 schematically shows the reference light modulating mechanism provided in the optical measuring instrument in the fifth embodiment. As illustrated in FIG. 6, the optical measuring instrument in the fifth embodiment is provided with a reference light modulating mechanism 30-5 constructed of two reflector driving mechanisms 31L, 31R, four reflectors $14a^+-14d^+$, position sensors $50a-50d$, and members 35L, 36R, $36_1$, $36_2$.

The reflector driving mechanisms 31L, 31R incorporate the same function of the reflector driving mechanism 31 provided in the optical measuring instrument in the first embodiment. To be specific, the reflector driving mechanisms 31L, 31R move the members 35L, 35R to positions instructed by the computer and, when instructed to start a fluctuation, control the positions of the members 35L, 35R so that the members 35L, 35R minutely fluctuate with the present positions being centered in accordance with the drive profile specifying data given to the mechanisms themselves.

At circular parts shown in FIG. 6, the members 35L, 35R or (members fitted with) the reflectors $14a^+-14d^+$ are rotatably fitted to the members $36_1$, $36_2$. Therefore, postures of the reflectors $14a^+-14d^+$ are controlled as they always remain unchanged irrespective of positions to which the members 35L, 35R move (even when angles of the members $36_1$, $36_2$ change). Namely, the reference light modulating mechanism 30-5 has such a structure that no matter how the members $36_1$, $36_2$ are tilted, the light beams from the lens systems 13a–13d are reflected by the reflectors $14a^+-14d^+$ and travel back to the lens systems 13a–13d.

The unillustrated computer is stored (set) with the data on fitting positions of the reflectors 14a+–14d+. Further, the computer, when operating based on the measurement sequence file creating program, creates the measurement sequence file stored with two pieces of drive profile specifying data, and the measurement condition data consisting of X- and Y-coordinates x, y and two Z-coordinates $z_1$, $z_2$ of the measuring points and the measuring time specifying data t.

Then, the computer in the present optical measuring instrument, when executing the control based on the measurement program, in step corresponding to step S104 (FIG. 2), instructs the reflector driving mechanism 31R to shift the measuring point relative to the reflector $14a^+$ to a position $z_{1i}$, and instructs the reflector driving mechanism 31L to shift the measuring point relative to the reflector $14d^+$ to a position $Z_{2i}$. Thereafter, the computer executes the same processes as those by the computer 51 in the optical measuring instrument in the first embodiment, and this sequentially obtains the measurement data about the four measuring points.

The optical measuring instrument in the fifth embodiment is also capable of simultaneously measuring data about the plurality of measuring points and is, as in the case of the optical measuring instruments in the first through third embodiments, capable of completing the measurement of the needed data in a short period of time.

<Sixth Embodiment>

An optical measuring instrument in accordance with a sixth embodiment has a modified structure of the optical measuring instrument in the fourth embodiment, in which a configuration of the reference light modulating mechanism and an operating procedure of the computer are different from those in the optical measuring instrument on the fourth embodiment.

Figure 7:
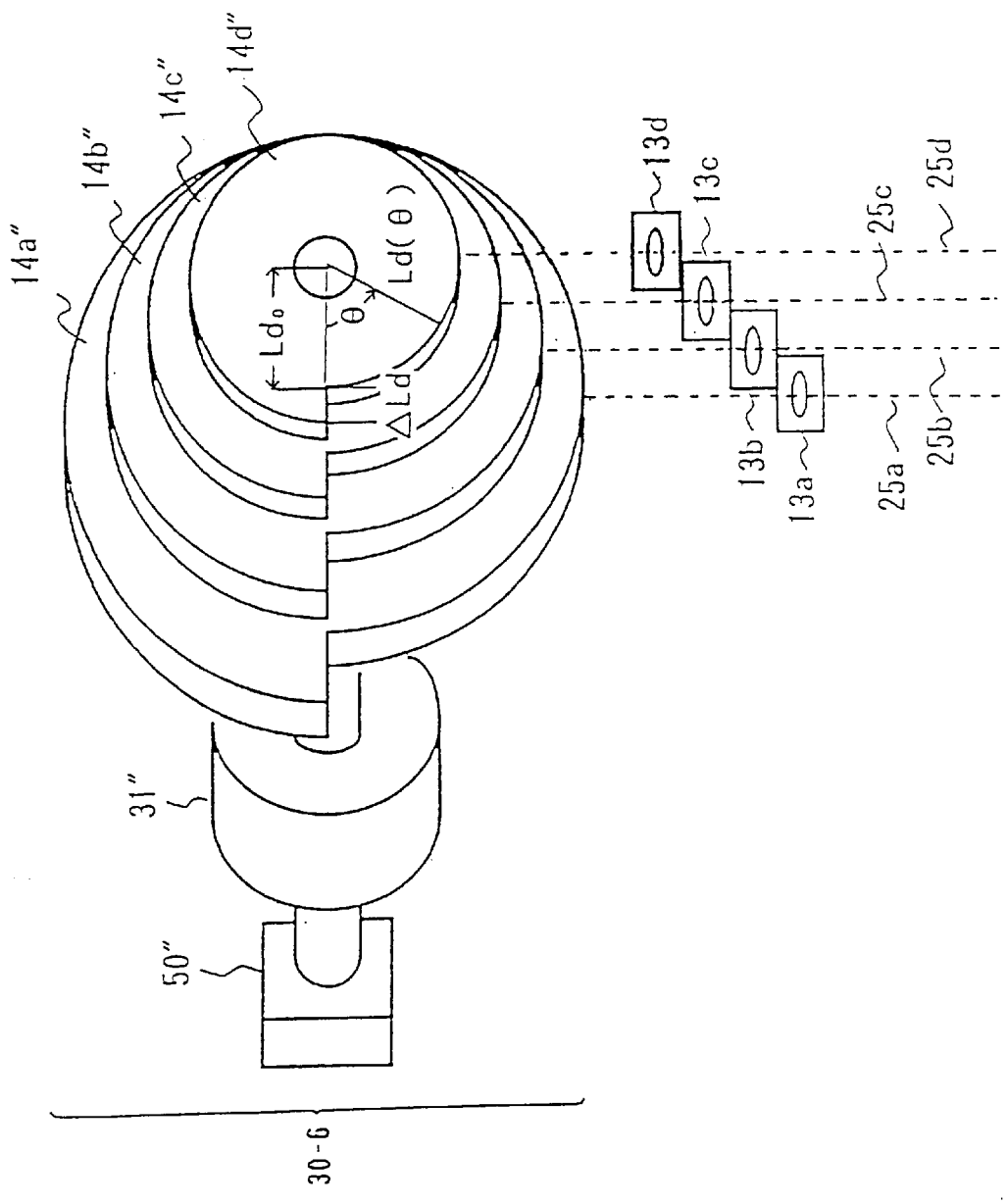
FIG. 7 is a diagram showing a configuration of a reference light modulating mechanism provided in an optical measuring instrument according to a sixth embodiment of the present invention.

FIG. 7 shows the configuration of the reference light modulating unit provided in the optical measuring instrument in the sixth embodiment. As illustrated in FIG. 7, the reference light modulating unit 30-6 in the sixth embodiment is constructed of reflectors $14a''$–$14d''$, a reflector driving mechanism 31", and a position sensor 50". The reflectors $14a''$–$14d''$ involve the use of plate-like members having centers of rotation, respectively, of which side surfaces are mirror surfaces, each assuming such a configuration that a distance from the center of rotation to the side surface changes in accordance with an angle of rotation. Specifically, as illustrated in FIG. 7, the reflector $14d''$ is composed of a member in which a distance $Ld(\theta)$ to the side surface disposed in a position of the rotation angle $\theta$ (unit is radian; $0 \leq \theta \leq 2\pi$) is expressed by $Ldo+\Delta Ld \cdot \theta/2\pi$) (which is the so-called curve of Archimedes). Then, the reflectors $14a''$–$14c''$ are composed of members of which lengths $La_0$, $\Delta La$, $Lb_0$, $\Delta Lb$, $Lc_0$, $\Delta Lb$ corresponding to $Ld_0$, $\Delta Ld$ are different from those of other reflector composing members.

A rotary shaft of a reflector driving mechanism 31" is connected to the center of rotations of the reflectors $14b''$–$14d''$. The position sensor 50" is also connected to a rotary shaft of a fixing member 53, and outputs data indicating an angle of rotation from the fiducial position of the rotary shaft.

The reflector driving mechanism 31" is controlled by the computer in the same way as the reflector driving circuit $31^{\#}$ in the fourth embodiment is controlled. Namely, the reflector driving mechanism 31" is given an angle-of-rotation range $\Delta\theta$ and a time variation pattern data of the angular speed as the drive profile specifying data. Then, the reflector driving mechanism 31", when instructed to move the reflectors to the position z, directs the side surface expressed by $\theta_0$ corresponding to z toward the lens system 13 by rotating the group of reflectors. Thereafter, when instructed to start the minute fluctuating operation, the rotary shaft is controlled so that the angle of rotation changes at an angular speed specified by the time variation pattern data and that the side surface of a range expressed by $\theta_0-\Delta\theta/2$~$\theta_0+\Delta\theta/2$ is directed toward the lens system 13.

The unillustrated computer is stored (set) with configuration data (such as $L_0$, $\Delta L$, etc.) of the reflectors $14a''$–$14d''$, and calculates the optical characteristic data at the four measuring points of which the depths are determined by values of $Lx_0+\Delta Lx \cdot \theta_0/2\pi$ ($x=a$–$d$) by use of those pieces of configuration data, the data outputted by the position sensor 50" and the data outputted by the A/D converter.

The optical measuring instrument in the sixth embodiment can also be used to simultaneously measure data associated with the plurality of measuring points and is, as in the case of the optical measuring instruments in the other preceding embodiments, able to complete the measurement of the needed data in a short period of time.

Note that the reflector driving mechanism 31" in the sixth embodiment involves the use of the mechanism for reciprocating the group of reflectors within a fixed angular range but may also uses a mechanism for rotating the group of reflectors. Even when using such a mechanism, the computer is capable of obtaining the information on the lengths of the optical paths of the respective reference light beams and the information for distinguishing the signals to which the reference light beams are related from the data outputted by the position sensor 50", and is therefore also able to calculate in parallel the optical characteristic data about the four measuring points in the different depths. Further, the configuration of each reflector is not limited to the configuration shown in FIG. 7, however, there may be adopted any configurations on condition that the computer is capable of recognizing, based on the data (corresponding to $\theta$) given from the position sensor 50", the lengths of the optical paths of the respective reference light beams which are formed at that point of time, and distinguishing, based on the data outputted by the A/D converter, the signals to which the reference light beams are related.

<Seventh Embodiment>

Figure 8:
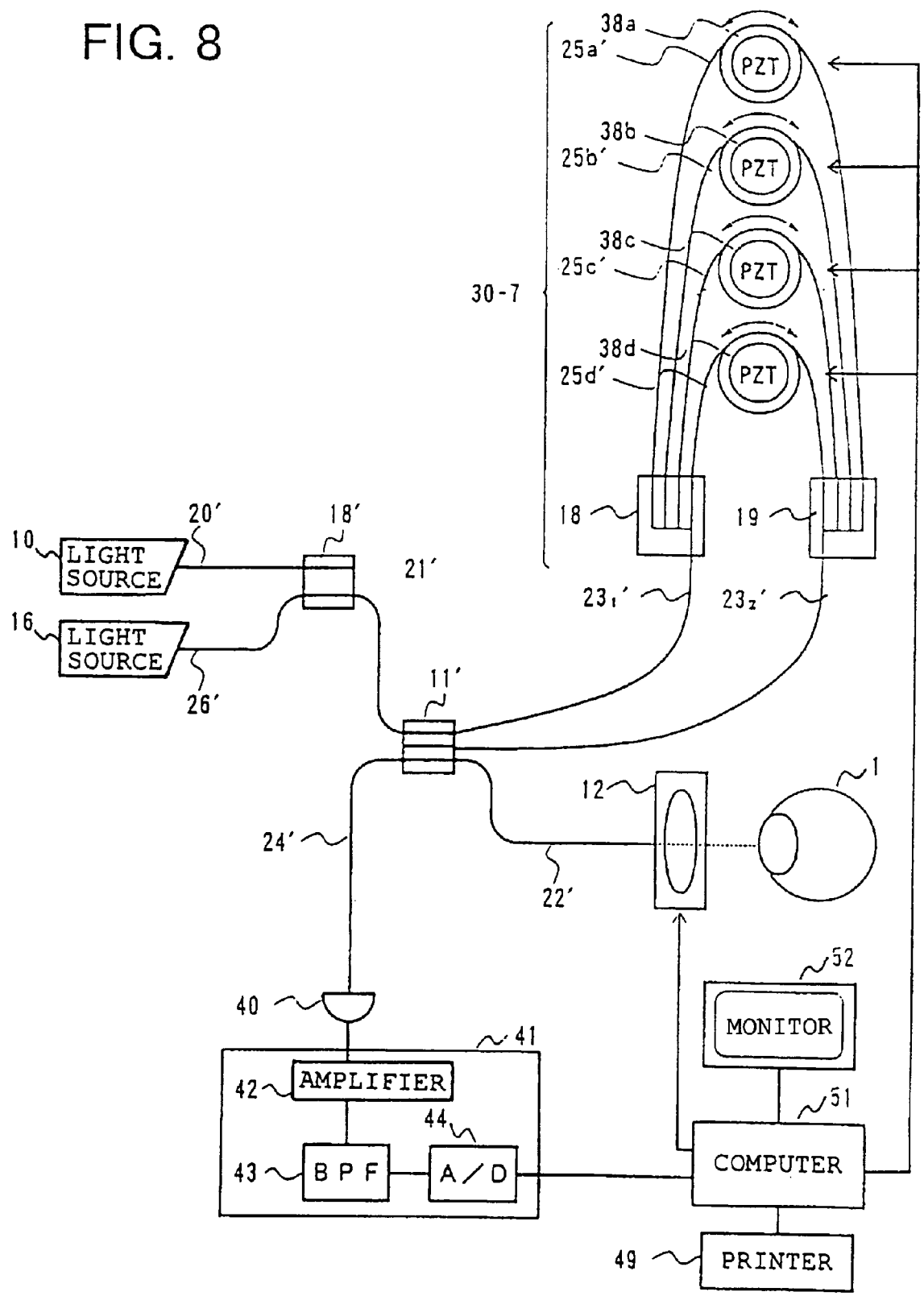
FIG. 8 is a diagram showing a construction of the optical measuring instrument in a seventh embodiment of the present invention.

FIG. 8 illustrates a construction of an optical measuring instrument in a seventh embodiment. In the seventh embodiment, an arrangement of the optical measuring instrument is similar to that of the first embodiment but a polarization-retaining fiber is adopted in each optical path, and having an arrangement of a reference light modulating unit 30-7. Therefore, the optical measuring instrument in the seventh embodiment uses a distribution coupling type optical multiplexer 17' and an optical multiplexer/demultiplexer 11' as substitutes for the (intensity split type) optical multiplexer 18 and optical multiplexer/demultiplexer 11 which utilizes the half-mirrors.

As shown in FIG. 8, the reference light modulating mechanism 30-7 in the present optical measuring instrument includes an optical demultiplexer 18, modulation mechanisms $38a$–$38d$, optical fibers $25a'$–$25d'$ each having a different length, and an optical multiplexer 19. The optical demultiplexer 18 demultiplexes the reference light inputted via an optical fiber light path $23_1'$ into four light beams, and supplies the optical fibers $25'$–$25d'$ with these light beams. The modulation mechanisms $38a$–$38d$ each is composed of a cylindrical piezo element (PZT) and a driving circuit thereof. The modulation mechanisms $38a$–$38d$ piezo elements) are respectively wound of some of the optical fibers $25'$–$25d'$. the other ends of the optical fibers $25a'$–$25d'$ are connected to the optical multiplexer 19. The optical multiplexer 19 multiplexes the light beams coming from the optical fibers 25a'–25d', and supplies the multiplexed light to the optical multiplexer/demultiplexer 11' via the optical fiber light path 23'. Namely, this optical measuring instrument involves the use of the reference light modulating mechanism 30-7 for modulating the reference light traveling through inside the optical fibers by applying outside forces to these optical fibers 25a'–25d'. The procedure by which the computer 51 controls the modulation mechanisms 38a–38d is basically the same as the procedure by which the computer 51 in the optical measuring instrument in the first embodiment controls the reflector driving mechanisms 31a–31d, and hence the explanation thereof is omitted.

The optical measuring instrument in the seventh embodiment is also capable of simultaneously measuring data about the plurality of measuring points and is, as in the case of the optical measuring instruments in the other preceding embodiments, able to complete the measurement of the needed data in a short period of time. Further, the optical measuring instrument in the seventh embodiment can be easily downsized because of using the optical fibers.

Note that the present optical measuring instrument is constructed by using the polarization retaining optical fibers, however, single-mode optical fibers may be of course used. The single-mode optical fiber is, however, inferior in terms of a polarization stability to the polarization retaining optical fiber, and hence, when using the single-mode optical fibers, it follows that the instrument easy to receive influences by a disturbance and a change in temperature is constructed. Therefore, when structuring the optical measuring instrument by use of the optical fibers, it is desirable that the polarization retaining optical fibers be used.

<Eighth Embodiment>

Figure 9:
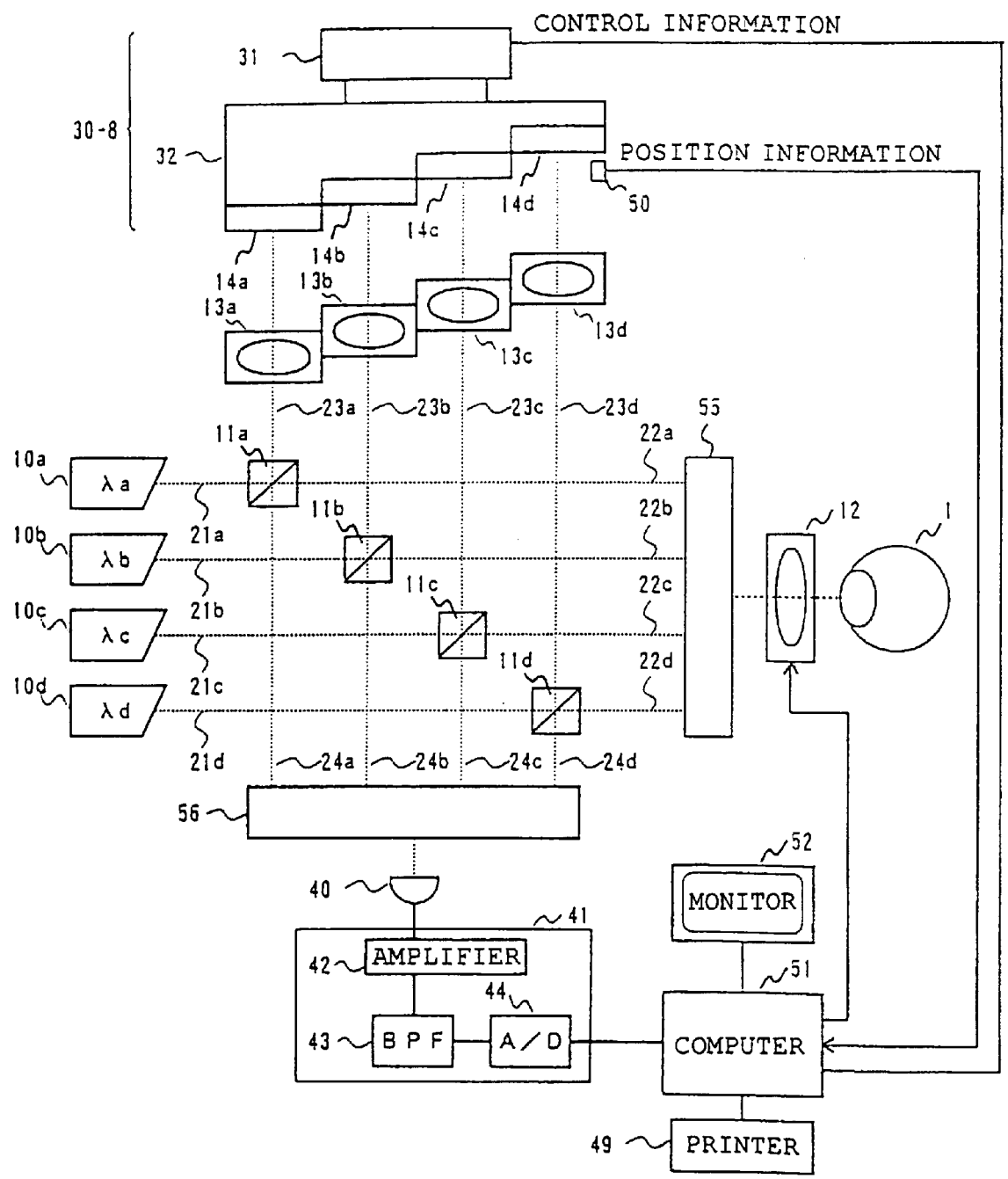
FIG. 9 is a diagram showing a construction of an optical measuring instrument according to an eighth embodiment of the present invention.

FIG. 9 shows a construction of an optical measuring instrument in an eighth embodiment. As illustrated in FIG. 9, the optical measuring instrument in the eighth embodiment includes four light sources 10a–10d. The light sources 10a–10d emit the short coherence length light beams having wave lengths $\lambda a$–$\lambda d$ different from each other.

An optical multiplexer/demultiplexer 11x classified as the same optical circuit as the optical multiplexer/demultiplexer 11 used in the first embodiment, is provided on an optical path 21x onto which the short coherence length light beams are emitted from the light sources 10x (x=a–d). Then, a multiplexer/demultiplexer 55 for multiplexing the wavelength is provided on an output side (on an optical path 22x) of the measurement light of the optical multiplexer/demultiplexer 11x.

The wavelength multiplexing multiplexer/demultiplexer 55 is an optical circuit for making the light beams with the multiplexed wavelengths $\lambda a$–$\lambda d$ of the short coherence length light beams coming from the optical multiplexers/demultiplexers 11a–11d travel toward the scan optical system 12, and making the light beams incident from the direction of the scan optical system 12 travel toward the optical paths 22 corresponding to these wavelengths. That is, the wavelength multiplexing multiplexer/demultiplexer 55 makes the light beam having the wavelength $\lambda a$ among the light beams incident from the side of the measurement object sample exit onto the optical path 22a, the light beam having the wavelength $\lambda b$ exit onto the optical path 22b, the light beams having the wavelength $\lambda c$ exit onto the optical path 22c, and the light beams having the wavelength $\lambda d$ exit onto the optical path 22d.

Lens systems 13a–13d are provided on the side of optical paths 24a–24d of the optical multiplexers/demultiplexers 11a–11d. A reference light modulating mechanism 30-8 constructed of the reflectors 14a–14d fixed to the member 32, the reflector driving mechanism 31 for driving the reflectors 14a–14d (the member 32) and the position sensor 50, is provided in a position upon which the reference light falls via the lens systems 13a–13d. Further, an optical multiplexer 56 is provided on the side of optical paths 23a–23d of the optical multiplexers/demultiplexers 11a–11d, and supplies a photoelectric converter 40 with the multiplexed light beams of the interference light beams coming from the optical multiplexers/demultiplexers 11a–11d.

Thus, the optical measuring instrument in the eighth embodiment is constructed so that the reflectors 14a–14d are driven at the same velocity by one single reflector driving mechanism 31, however, the reference light beams incident on the reflectors have different wavelengths. Namely, moving velocities of the reflectors are the same, however, modulation patterns effected on the reference light beams are different. Therefore, the output of the photoelectric converter 40 contains signals taking such a form that magnitudes of the reflected light components from the four measuring points in the different depths can be distinguished as in the case of the optical measuring instruments in the preceding embodiments. The computer 51 processes the output from the A/D converter 44 by the same procedure as that of the computer 51 in the optical measuring instrument in the first embodiment, thereby simultaneously obtaining the optical characteristic data about the four measuring points.

Incidentally, as a matter of course, the optical measuring instrument may be structured so that four photoelectric converters for receiving the light beams outputted from the optical multiplexers/demultiplexers 11a–11d are provided without providing the optical multiplexer 56, then a circuit (as used in the signal processing circuit in the second embodiment) constructed of an amplifier, a BPF, a rectifier, a LPF, a logarithmic amplifier or an amplifier and an A/D converter, is provided posterior to each of the photoelectric converter, and the output of each A/D converter is supplied to the computer.

<Ninth Embodiment>

Before explaining an optical measuring instrument in a ninth embodiment, a construction and an operation of an optical modulating device 110 used in the optical measuring instrument in the ninth embodiment will be described.

Figure 10:
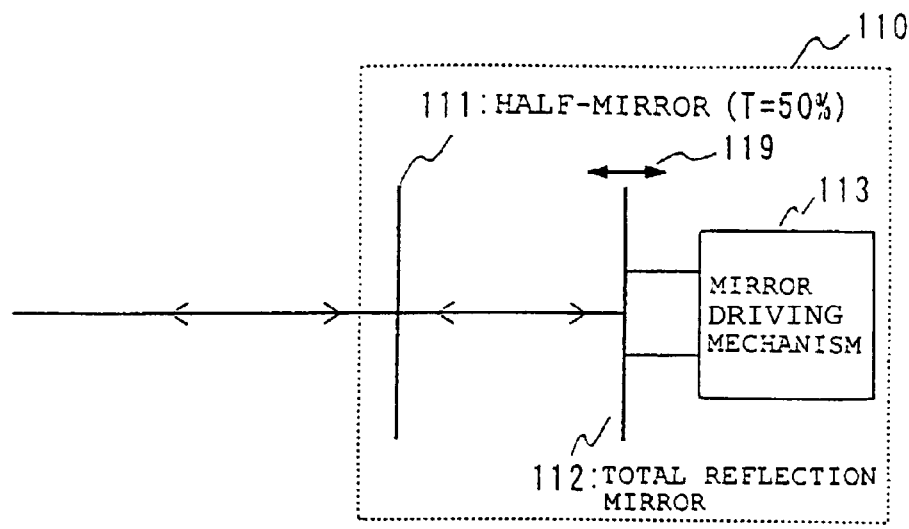
FIG. 10 is a diagram showing a configuration of an optical modulating device provided in an optical measuring instrument according to a ninth embodiment of the present invention.

As shown in FIG. 10, the optical modulating device 110 includes a mirror driving mechanism 113 and a total reflection mirror 112 fitted to the mirror driving mechanism 113. The mirror driving mechanism 113 moves the total reflection mirror 112 in an arrow direction 119 (a direction of normal line), and is attached to a base plate of the optical modulating device 110. Further, the optical modulating device 110 has a half-mirror 111 fitted to the base plate and disposed parallel with the total reflection mirror 112. Note that in the optical modulating device 110, the mirror driving mechanism 113 involves the use of a mechanism constructed of a piezo element and a control circuit thereof, and a half-mirror exhibiting a transmissivity T of 50% is used as the half-mirror 111.

Figure 11:
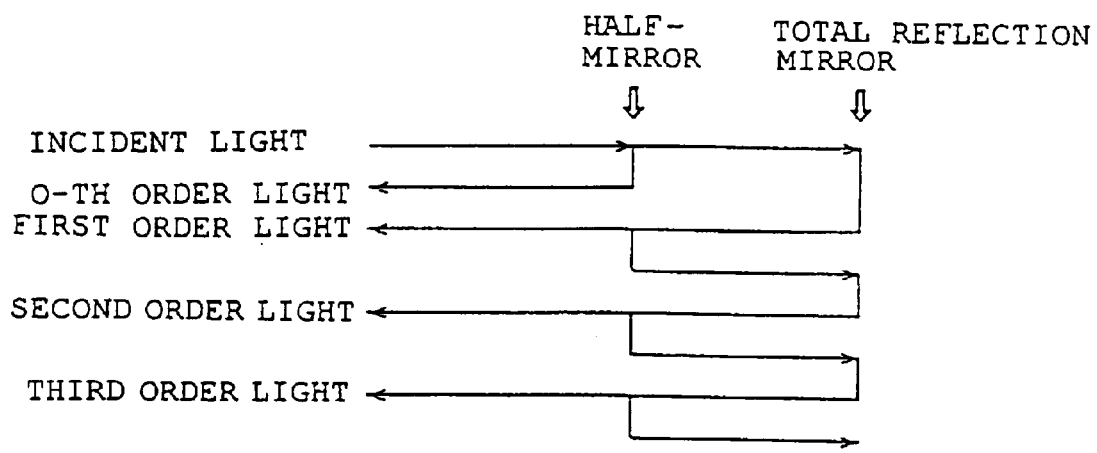
FIG. 11 an explanatory diagram showing an operation of the optical modulating device provided in the optical measuring instrument according to the ninth embodiment of the present invention.

That is, the optical modulating device 110 is structured to output, when the light is, as schematically shown in FIG. 11, incident at an incident angle of "0" degree upon the half-mirror 111, 0-th order light beams reflected as some proportion of the incident light by the half-mirror 111, and i-th order light beams reflected "i" times (i=1, 2, 3, . . . ) as some of the incident light by the total reflection mirror 112.

Figure 12:
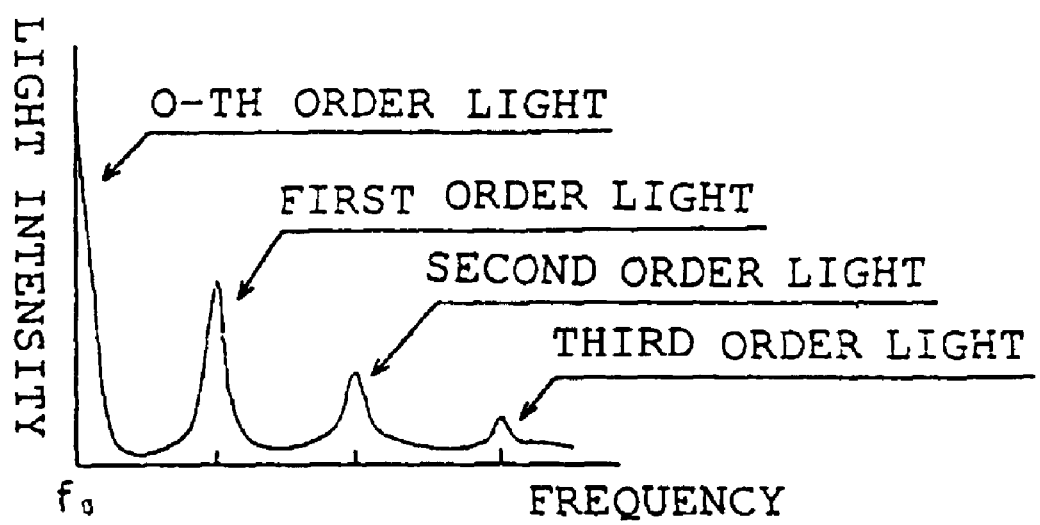
FIG. 12 is a diagram showing a spectrum of the light outgoing from the optical modulating device provided in the optical measuring instrument according to the ninth embodiment.

Then, since the half-mirror 111 having the transmissivity T of 50% is used herein, for example, the laser beams having a frequency $f_0$ are incident at the incident angle of "0" degree upon the half-mirror 111, and, if the total reflection mirror 112 is moved at a fixed velocity V by use of the mirror driving mechanism 113, it follows that the optical modulating device 110 outputs the light with a spectrum as illustrated in FIG. 12.

Namely, the 0-th order light beams are not influenced by a motion of the total reflection mirror 112, and hence the light beams having the same frequency as the frequency $f_0$ of the incident light are outputted as the 0-th order light beams. On the other hand, a length of the optical path of the i-th order light beams (i=1, 2, . . . ) reflected "i" times by the total reflection mirror 112, changes at avelocity V·i. Hence, the light beams shifted by $\Delta f \cdot i$ from the frequency $f_0$ are outputted as the i-th order light beams. Note that $\Delta f$ is a constant of which a value is determined in accordance with the moving velocity V of the total reflection mirror 112.

Further, since the transmissivity T of the half-mirror 111 is 50%, the i-th order (i=1, 2, . . . ) outputted from the optical modulating device 110 come to have an intensity that is ½ as small as (i−1)th order light beams. (An intensity I of the i-th order light beams outputted from the optical modulating device 110 is given by $I=I_0 \cdot T'^2(1-T')^{i-1}$, where T'=T/100, and $I_0$ is the intensity of the incident light on the assumption that each mirror is an ideal mirror.) Moreover, let d(t) be a spacing between the half-mirror 111 and the total reflection mirror 112 at a certain time t, the i-th order light beam at the time t has a difference 2d(t) of the optical path length from that of the (i−1)th order light beam.

Thus, the optical modulating device 110 is capable of generating (outputting) the light containing the plurality of light components of which the frequencies and the optical path lengths are different from each other.

Given hereinafter is an explanation of a construction and an operation of the optical measuring instrument in the ninth embodiment, which is constructed by use of the optical modulating device 110.

Figure 13:
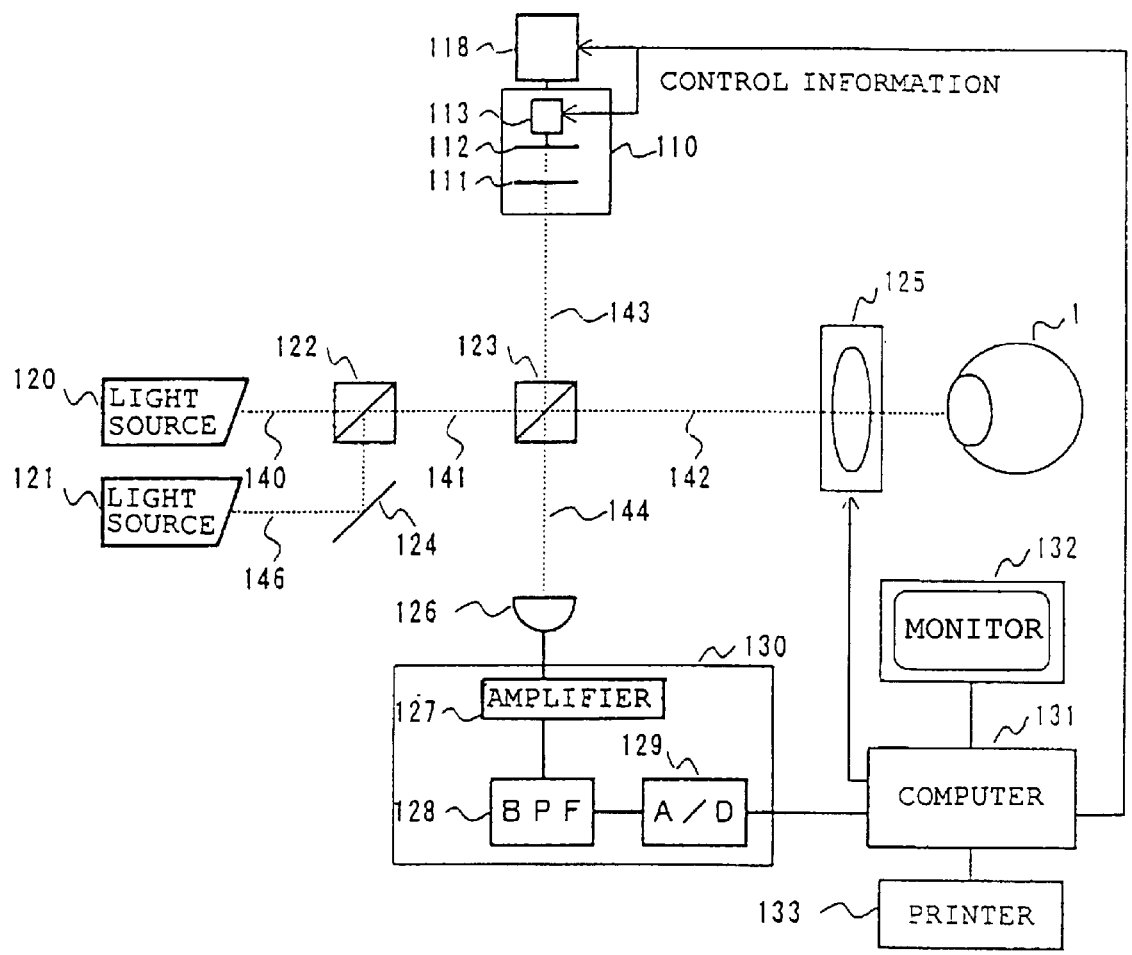
FIG. 13 is a block diagram showing a construction of the optical measuring instrument according to the ninth embodiment.

FIG. 13 illustrates a construction of the optical measuring instrument in the ninth embodiment. The optical measuring instrument in the ninth embodiment is structured as an OCT instrument for a measurement of an eye and, as illustrated therein, includes a light source 120 and a light source 121.

The light source 120 emits beams of light used for the measurement, and is constructed by use of a super luminescence diode (SLD) for emitting light beams of which a wavelength is approximately 830 nm and a coherence length is approximately 10 μm (which is hereinafter referred to as short coherence length light). Note that the reason why the light beams having the wavelength of 830 nm are used for the measurement is that the light beams in a near infrared ray region do not give damages to the eye to be measured, and exhibit a high penetrance into the tissues. Further, the light source 120 is capable of ON-OFF control by use of digital signals and connected to a computer 131 via an unillustrated signal line.

The light source 121 emits visible light beams and is constructed of a semiconductor laser for emitting light beams having a wavelength of 633 nm.

An optical multiplexer 122 is provided on an optical path 140 along which the light source 120 outputs the short coherence length light beams. Further, a total reflection mirror 124 is provided on an optical path 146 along which the light source 121 outputs the visible light beams.

The optical multiplexer 122 is a half-mirror-utilized optical circuit which makes the light beams incident from the side of the optical path 140 travel straight directly (toward an optical path 141), and guides the light beams incident from downward in the Figure toward the optical path 141. The light source 121 and the total reflection mirror 124 are disposed with respect to the optical multiplexer 122 so that the light beams coming from the light source 121 are guided onto the optical path 141.

To be more specific, the light source 121, the total reflection mirror 124 and the optical multiplexer 122 are defined as components for guiding the visible light beams (which are so-called aiming beams) onto the same optical path as that of the short coherence length light beams. The light source 121 is driven when confirming that a target position of a measurement sample 1 is irradiated with the short coherence length light beam. Accordingly, if the light beam in the visible light region is used as the short coherence length light beam (if the object for measurement may be irradiated with such a light beam), the optical measuring instrument can be constructed without providing those components. Further, in the case of using a CCD camera for making visible the short coherence length light beams reflected and scattered within the measurement object sample and making an observation, the optical measuring instrument can be constructed without providing those elements.

An optical multiplexer/demultiplexer 123 is provided on the optical path 141. The optical multiplexer/demultiplexer 123 is also an optical circuit utilizing a half-mirror. The optical multiplexer/demultiplexer 123 demultiplexes the short coherence length light beams incident from the side of the optical path 141 and deflects the light beams onto an optical path 142 and an optical path 143. The optical multiplexer/demultiplexer 123 also couples (multiplexes) the light beams incident from the sides of the optical paths 142, 143 and converges the light beams onto an optical path 144. Hereinafter, among the short coherence length light beams demultiplexed by the optical multiplexer/demultiplexer 123, the light beams traveling onto the optical path 142 are termed measurement light beams, the light beams traveling onto the optical path 143 are referred to as reference light beams, and the light beams traveling onto the optical path 144 are called interference light beams.

A scan optical system 125 is provided on the optical path 142. The scan optical system 125 incorporates a mechanism for shifting a target position (a measuring position) of the measurement light beams. The scan optical system 125, of which an operation can be controlled by an external device, is controlled by signals transmitted from a computer 131.

An optical modulating device 110 to which a position control mechanism 118 is connected, is provided on an optical path 143. The position control mechanism 118 is a mechanism for changing a distance between the optical modulating device 110 and the optical multiplexer/demultiplexer 123, and operates in accordance with control information given from a computer 131.

A photoelectric converter 126 for outputting a current signal assuming a level corresponding to an intensity of the incident light is provided on the side of the optical path 144. A signal processing circuit 130 constructed of an amplifier 127, a BPF (Band-Pass Filter) 128 and an A/D converter 129 is provided posterior to the photoelectric converter 126. An output of the A/D converter 44 is supplied to the computer 131.

The photoelectric converter 126 is a circuit composed of an avalanche photo diode and a driving circuit thereof. The electric signal assuming the level corresponding to the intensity of the interference light outputted by the photoelectric converter 126 is converted into a voltage signal and amplified by the amplifier 127 in the signal processing circuit 130. The BPF 128 passes only an AC component, contained in the voltage signal outputted by the amplifier 127, of which a frequency exists in a predetermined region. A pass band of the BPF 128 is set to one that corresponds to the drive profile specifying data that may be supplied to the mirror device mechanism 113 (the content of the drive profile specifying data which can be given to the mirror driving mechanism 113 is restricted depending on the pass band of the BPF 128). The A/D converter 129, under the control of the computer 131, executes a process of converting an analog voltage signal outputted by the BPF 128 into a digital signal.

The computer 131 is stored with a measurement sequence file creating program, a measurement program, a data processing program, and data on the lengths of the optical paths when the optical modulating device 110 is in the fiducial position.

Among the programs stored in the computer 131, the measurement sequence file creating program is a program for creating in an interactive format a measurement sequence file containing drive profile specifying data (which will be explained in details later on), three-dimensional coordinate data on several points to be measured, and measurement time specifying data of respective measuring points. Further, the measurement program is started up when performing an actual measurement. The computer 131, when the measurement program is started up, recognizes measurement conditions and procedures based on the data in the measurement sequence file designated by the operator, and measures optical characteristic data about the respective measuring points. The computer 131 creates the measurement data file stored with the measurement results, and then finishes the measurement program. Moreover, the data processing program serves to output to a monitor 132 or a printer 133 the data stored in the measurement data file in the form of two- and three-dimensional images or raw data.

A general operation of the optical measuring instrument will hereinafter be described.

The person (operator) who performs the measurement by use of the present optical measuring instrument creates several (at least one) measurement sequence files by running the measurement sequence file creating program in advance of an actual measurement, and stores the files in the computer 131.

The drive profile specifying data set in the measurement sequence file serves to specify the drive profile of the total reflection mirror 112 by the mirror driving mechanism 113, and consists of a category specifying data for showing a category of the drive profile, cycle data for specifying a cycle, and data for specifying an amplitude. In the optical measuring instrument, data in which a position of the total reflection mirror 112 changes in a configuration of sine wave with respect to the time, data in which the position changes in a configuration of triangular wave and a serrated configuration, and the like are prepared as the category specifying data. Further, standard values are prepared as the cycle data and the amplitude data, and the operator determines the drive profile specifying data (stores the same data in the measurement sequence file) used for the measurement by combining the respective pieces of data. Note that the standard value of the amplitude data is an extremely small value (with which the total reflection mirror 112 oscillates minutely, as will be described in detail).

Further, the operator sets, in the measurement sequence file, a necessary quantity of measurement condition data consisting of X-, Y- and Z-coordinates x, y, z of the measuring point and measuring time specifying data t. Herein, the Z-coordinates are coordinates set in a depthwise direction of the measuring point, and the X- and Y-coordinates are orthogonal coordinates set on the plane perpendicular to the depthwise direction.

Then, the operator, when starting the actual measurement, runs the measurement program.

The computer 131 having started the operation based on the measurement program, to begin with, issues an initializing command to the scan optical system 125, thereby setting a state of the scan optical system 125 as a fiducial state. Namely, the computer 131 sets the position (X, Y) in which to introduce the measurement light as a fiducial position $(x_o, y_o)$.

Subsequently, the computer 131 shifts to a standby status for inputting a name of the measurement sequence file from the operator. Then, when the name of the measurement sequence file is inputted, the computer 131 reads the drive profile specifying data stored in the specified measurement sequence file, and element data $x_i, y_i, z_i, t_i$ (i=1−Nmax) in each piece of subsequent measurement condition data. Next, the computer 131 notifies the control circuit in the mirror driving mechanism 113, of the drive profile specifying data, and stands by till an operation of instructing the start of the measurement is done.

On the other hand, the operator, after running the measurement program, inputs the name of the measurement sequence file for use. Then, the operator adjusts a position of the measurement object sample 1 and a position of the optical measuring instrument while confirming the position irradiated with the measurement light by switching ON the light source 121, whereby the measurement object sample 1 and the optical measuring instrument take a predetermined relative positional relationship. Then, upon finishing the adjustment of the positional relationship, the operator switches OFF the light source 121 and instructs the computer 131 to start the measurement.

Figure 14:
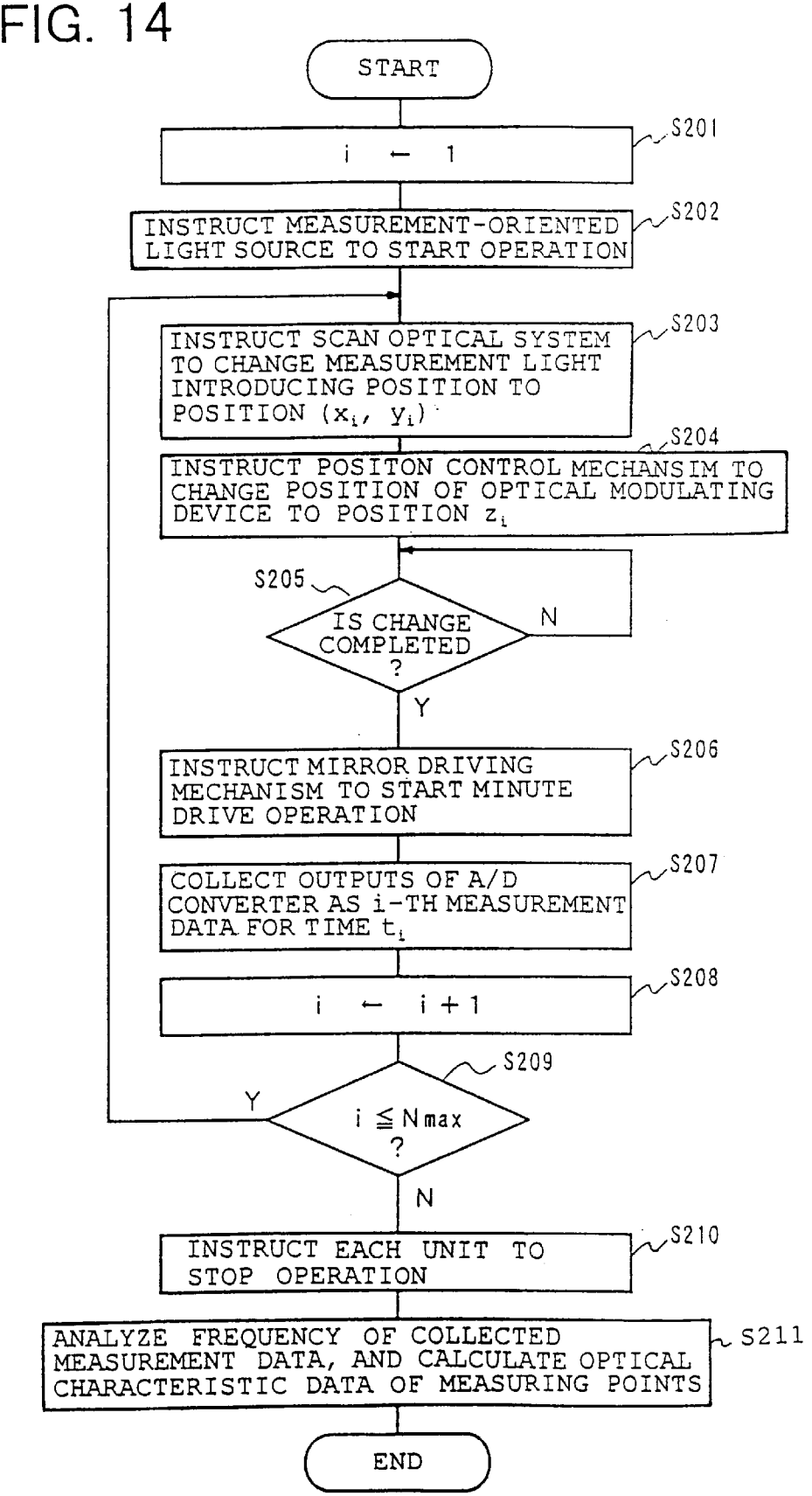
FIG. 14 is a flowchart showing an operating procedure of a computer incorporated into the optical measuring instrument according to the ninth embodiment.

The computer 131 instructed to start the measurement operates in accordance with a flowchart shown in FIG. 14.

To be specific, the computer 131 at first sets "1" in a variable i (step S201), and instructs the light source 120 (for the measurement) to start the operation (an emission of the short coherence length light beams) (step S202). Further, the computer 131 displays a frame of graph for displaying the measured results on the monitor 132.

Subsequently, the computer 131 instructs the scan optical system 125 to change the measurement light introducing position to a position $(x_i, y_i)$ (step S203). Further, the computer 131 instructs the position control mechanism 118 to shift central position of the optical modulating device 110 to position $z_i$ (step S204).

After finishing step S204, the computer 131 stands by till information showing a completion of the positional change is inputted from the device having been given the instruction (step S205) (if there is no device having been given the instruction, step S105 comes to an end without waiting for the input of the information). Then, when receiving the notifications from all the devices having been given the instruction (step S205; Y), the computer 131 instructs the control circuit of the mirror driving mechanism 113 to start the minute drive operation (a drive control operation based on the drive profile specifying data) (step S206). Then, the computer 131 starts a process of cyclically obtaining the data from the A/D converter 129, and stores the obtained data as i-th measurement data (step S207).

Then, the computer 131, after executing such a process for a time $t_i$, instructs the mirror driving mechanism 113 to halt the minute driving operation, and finishes step S207.

After the termination of step S207, the computer 131 increments a content of the variable i by "1" (step S208), and, if i≦Nmax (step S209; Y), re-executes the processes from step S203 in order to make the next measurement. Whereas if i>Nmax, (step S209; N), the computer 131 instructs the measurement-oriented light source 120, etc., to stop the operation (step S210).

Thereafter, the computer 131 analyzes a frequency of each piece of measurement data obtained in step S207 in consideration of the contents of the drive profile specifying data, and calculates and stores optical characteristic data about (K×Nmax) measuring points (step S211). Then, the processes shown therein are ended.

Namely, the light outputted by the optical modulating device 110 contains a plurality of light beams of which frequencies and optical path lengths are different from each other (see FIG. 12), and therefore one piece of measurement data on the measuring point in a depth $z_i$ obtained in step S207 contains data by which to obtain optical characteristic data about measuring points having depths $z_i$, $z_i+d$, $z_i+2d$, . . . $z_i+(K-1)d$. In step S211, a process of obtaining the optical characteristic data about the measuring points in these depths from one piece of measurement data on the measuring point having the depth zi, is executed for each "i" of 1–Nmax. Note that "d" is a value (a difference in optical path length between the (i+1)th order light beam and the i-th light beam) determined by a geometry of the mirrors in the optical modulating device 110, and K is a value of integer determined from a measurement accuracy needed.

Thus, the present optical measuring instrument is capable of simultaneously acquiring the optical characteristic data of the multiplicity of measuring points each having a different depth, and is therefore able to complete the measurement in a short period of time. Further, the optical modulating device 110 is used as the mechanism for generating the plural reference light beams each having a different frequency. Hence, the present optical measuring instrument can be manufactured in a more compact configuration at lower costs than the optical measuring instruments in the other preceding embodiments discussed so far.

Incidentally, in the optical measuring instrument in the ninth embodiment, the total reflection mirror 112 is minutely fluctuated by the mirror driving mechanism 113, and the whole optical modulating device 110 is moved by the position control mechanism 118, which aims at not making it possible to simultaneously obtain the optical characteristic data of the plurality of measuring points having the different depths but making it feasible to perform the measurement in a state where the positions of the measuring points are substantially fixed. In other words, what is needed for attaining the simultaneous acquisition of the optical characteristic data about the plurality of measuring points having the different depths is only to move the total reflection mirror 112 in the optical modulating device 110. It is therefore possible to obtain the optical measuring instrument capable of simultaneously measuring the plurality of measuring points different in depths even when structured to shift the wavelengths of the reference light beams together with the shifts of the measuring points simply by the mirror driving mechanism 113 moving the total reflection mirror 112.

Further, the optical measuring instrument in the ninth embodiment involves the use of the optical measuring device 110 in which the total reflection mirror 112 is moved, however, the optical measuring instrument incorporating absolutely the same functions can be acquired even by use of the optical modulating device in which the half-mirror 111, or the half-mirror 111 and the total reflection mirror 112 is/are moved.

<Tenth Embodiment>

An optical measuring instrument in a tenth embodiment has a difference in terms of only a construction of the optical modulating device used herein from the optical measuring instrument in the ninth embodiment. Therefore, herein, the description will concentrate on an optical modulating device 110b employed in the optical measuring instrument in the tenth embodiment.

Figure 15:
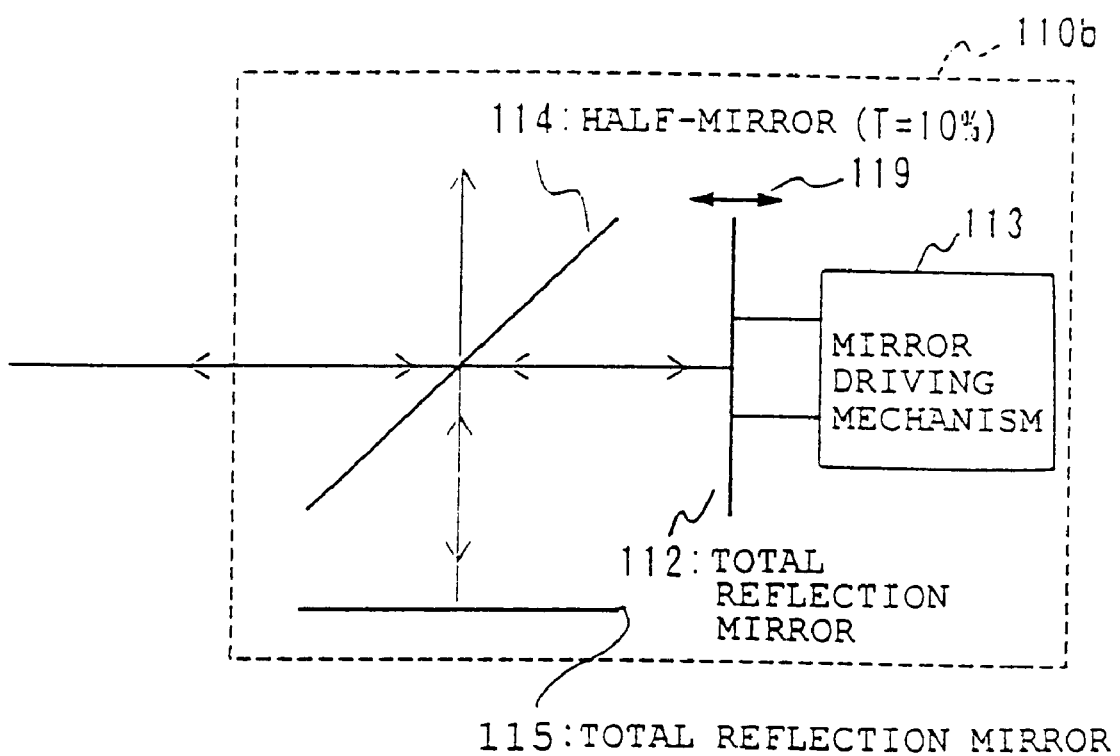
FIG. 15 is a diagram showing a configuration of an optical modulating device provided in an optical measuring instrument according to a tenth embodiment.

As shown in FIG. 15, the optical modulating device 110b includes the mirror driving mechanism 113 and the total reflection mirror 112 fitted to the mirror driving mechanism 113. The mirror driving mechanism 113 moves the total reflection mirror 112 in the arrow direction 119 (the direction of normal line), and is attached to a base plate of the optical modulating device 110b. Further, the optical modulating device 110b has, in a layout shown therein, a half-mirror 114 and a total reflection mirror 115 respectively fitted to the base plates. Note that in the optical modulating device 110b, the mirror driving mechanism 114 involves the use of a mechanism constructed of a piezo element and a control circuit thereof, and a half-mirror exhibiting a transmissivity T of 10% is used as the half-mirror 114.

Figure 16:
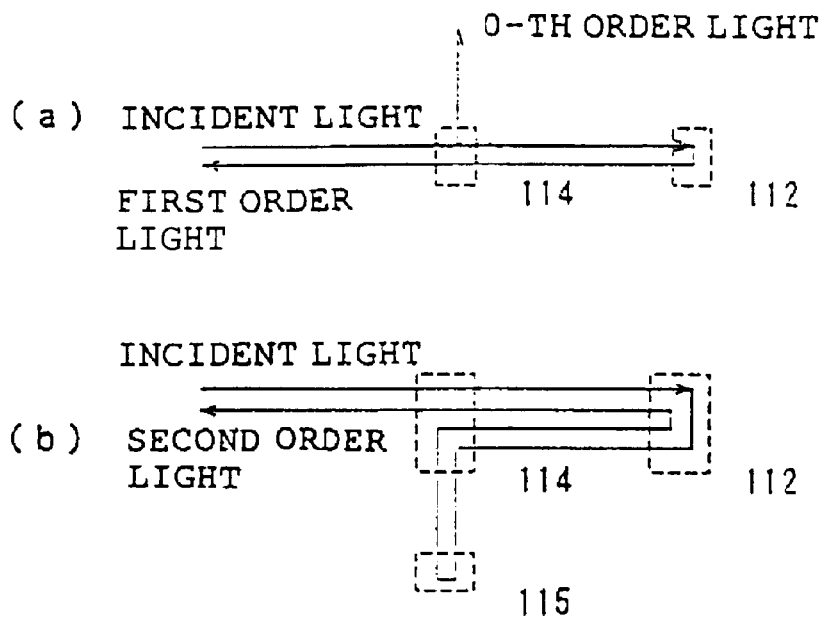
FIG. 16 is an explanatory diagram showing an operation of the optical modulating device shown in FIG. 15.

That is, the optical modulating device 110b is structured to output, when the light is, as schematically shown in FIGS. 16(a) and 16(b), incident at an incident angle of 45 degrees upon the half-mirror 114, 0-th order light beams reflected as some proportion of the incident light by the half-mirror 114, and i-th order light beams reflected "i" times (i=1, 2, . . . ) as some of the incident light by the total reflection mirror 112.

Figure 17:
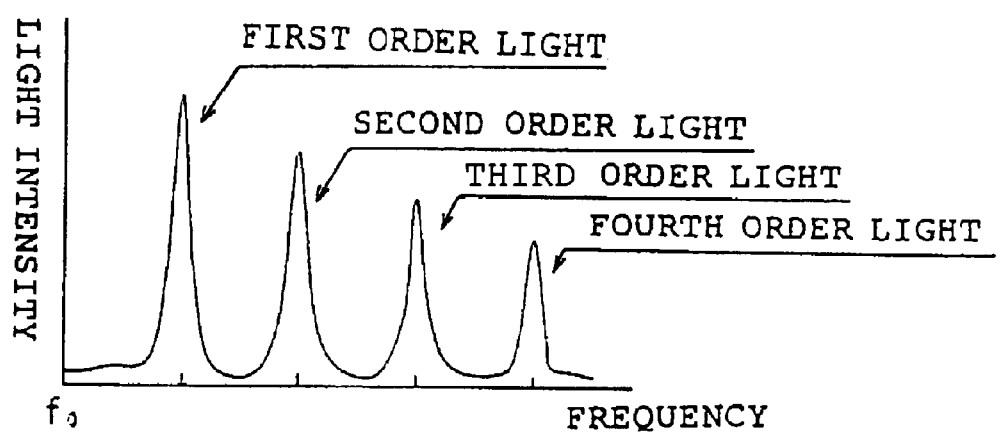
FIG. 17 is a diagram showing a spectrum of the light outgoing from the optical modulating device shown in FIG. 15.

Then, since the half-mirror 114 having the transmissivity T of 10% is used herein, for example, the laser beams having a frequency $f_0$ are incident at the incident angle of 45 degrees upon the half-mirror 114, and, if the total reflection mirror 112 is moved at a fixed velocity V by use of the mirror driving mechanism 113, it follows that the optical modulating device 110b outputs the light with a spectrum as illustrated in FIG. 17 onto the same optical axis as that of the incident light.

Namely, the 0-th order light beams (having the frequency $f_0$), which are not reflected by the total reflection mirror 112, do not travel back onto the same optical axis as that of the incident light (see FIG. 16(a)), and are not therefore outputted from the optical modulating device 110b.

Further, the i-th order light beams (i=1, 2, . . . ) reflected "i" times by the total reflection mirror 112 are outputted as the light beams having a frequency $f_0+\Delta f \cdot i$ from the optical modulating device 110b. Then, since the transmissivity T of the half-mirror 114 is 10%, the i-th order light beams (i=1, 2, . . . ) outputted from the optical modulating device 110b have an intensity that is approximately 80% of the (i−1)th order light beams. (An intensity I of the i-th order light beams of the optical modulating device 110b is given by $I=I^0 \cdot T'^2(1-T')^{2i-2}$, where T'=T/100, and $I_0$ is the intensity of the incident light on the assumption that each mirror is an ideal mirror.) Moreover, letting d(t) be a sum of a distance between the half-mirror 114 and the total reflection mirror 115 and a distance between the half-mirror 114 and the total reflection mirror 112 at a certain time t, the i-th order light beam at the time t has a difference $2d(t)$ of the optical path length from that of the (i−1)th order light beam (See FIG. 16).

Thus, the optical modulating device 110b is capable of generating the light containing not the light beams having the same frequency as that of the incident light but the plurality of light components of which the frequencies and the optical path lengths are different from each other. The optical measuring instrument in the tenth embodiment is constructed by use of the optical modulating device 110b.

Therefore, the optical measuring instrument in the tenth embodiment can be manufactured in the compact configuration at the low costs as in the case of the optical measuring instrument in the ninth embodiment.

Moreover, the present optical measuring instrument obtains the optical characteristic data by utilizing the interference of the short coherence length light, and hence it is not required that the light outputted from the optical modulating device should contain the light component having the same frequency as that of the measurement light. Then, it follows that the light received by the photoelectric converter 126 contains, when the above light component having the same frequency is not contained, a greater quantity of light components used for calculating the optical characteristic data. Accordingly, it may be conceived as a better option from that point of view that the optical measuring instrument be structured by using the optical modulating device 110b. In terms of a minimum value (a spacing between the measuring points to be measured simultaneously) of the difference between the optical path lengths which can be given between the light components contained in the output of the optical modulating device and of an entire size of the instrument, however, it may be another better option that the optical measuring instrument be structured by using the optical modulating device 110.

<Modified Embodiments>

The optical measuring instruments in the embodiments discussed above can be modified in a variety of forms. For instance, the optical measuring instrument in each of the third through eighth embodiments may be structured by using the signal processing circuit employed in the optical measuring instrument in the second embodiment.

Further, a corner cube, a cat eye, and the like may also be used instead of the reflector 14 constructed of the total reflection mirror.

Moreover, the optical measuring instrument in each of the embodiments discussed above uses the SLD as a light source for the measurement, however, any types of light sources are usable if capable of emitting the light having the short coherence length as a result. For example, there can be used a light emitting diode (LED), a pulse/laser light source, an incandescent light source, a light source constructed by combining a continuous oscillation laser with a poor interference, a laser oscillated by an electric current not exceeding a threshold current and a plurality of multi-mode lasers, and a laser-excited fluorescent light source. Further, there may also be used a light source, for emitting the short coherence length light, constructed by adding to a coherent light source such as a laser a device for causing an irregular jump in phase by modulating the output light thereof at random.

Moreover, in the optical measuring instrument in the fourth embodiment, etc., the same mechanism is used for changing the length of the optical path of the reference light (moving the measuring point) and for modulating the reference light. The optical measuring instrument may be, however, constructed by separately providing a mechanism for moving the measuring point. That is, the moving mechanism used in the optical measuring instrument in the third embodiment may be added to the optical measuring instrument in the fourth embodiment. Further, the optical measuring instrument may also be structured so that the length of the optical path of the reference light is changed by providing a pair of reference light oriented fibers with their edge surfaces facing to each other in a part of the optical path of the reference light and adjusting a spacing between the edge surfaces of the pair of reference light oriented fibers, or alternatively a frequency of the reference light may also be modulated by minutely changing the spacing therebetween. Moreover, a mechanism for changing the length of the optical path may be provided not on the side of the reference light but on the side of the measurement light.

Further, the mechanism for modulating the reference light is not confined to what is shown in each of the embodiments, however, e.g., a mechanism using an acoustic optical element may also be adopted. Furthermore, it is also feasible to modulate the reference light in patterns different from each other, which involves disposing optical media each individually exhibiting a distribution of refractive indexes on the optical paths of the reference light beams (or, alternatively, disposing one single optical medium across all the optical paths), and changing relative position(s) of those or that optical medium with respect to the optical path of the reference light.

Further, the optical measuring instrument may be constructed so that both of the frequency and an amplitude of the reference light are modulated, or only the amplitude is modulated. Moreover, the optical measuring instrument may be structured so that a polarizing plane rotator based on a magnetic field such as a Faraday element is provided on each optical path of the reference light, and the reference light is thereby modulated in such a form as a rotation (modulation) of the polarizing plane.

Further, the optical measuring instrument may be constructed so that not only the reference light but also the measurement light are modulated. For example, the optical measuring instrument may be constructed in such a way that the amplitude modulation element, etc., is further provided on the side of the measurement optical path to modulate the amplitude of the measurement light, and, as a result of modulating the frequency of the reference light and the amplitude of the measurement light, the light containing the information on the plurality of measuring points in a distinguishable form exits the optical multiplexer/demultiplexer.

The optical measuring instruments in the first to eighth embodiments are capable of simultaneously measuring the four measuring points, however, the optical measuring instrument may also be, as a matter of course, constructed so that a plurality of measuring points excluding the above four measuring points can be measured at the same time.

Moreover, in the optical measuring instruments in the embodiments discussed above, the variation quantity of length of the optical path of the reference light is so controlled as not to exceed the coherence length of the short coherence length light outputted by the light source. As in the case of the prior art optical measuring instrument, however, the optical measuring instrument may be of course constructed so that the wavelength of the reference light is shifted with the movement of the measuring point by changing the length of the optical path of the reference light in a predetermined pattern. If constructed in this way, however, a degree of freedom of the measurement might become lower than that of the optical measuring instrument in each of the embodiments discussed above (a measuring sequence, etc., might be restricted).

The optical measuring instrument in the tenth embodiment uses the optical modulating device 110b structured to move the total reflection mirror 112. The optical measuring instrument may be, however, actualized by use of an optical modulating device contrived to move the total reflection mirror 112 and the total reflection mirror 115 together.

Further, the optical measuring instrument can be manufactured by using the optical modulating device contrived to move the half-mirror 114 or the total reflection mirror 115. In this case, however, it follows that the light outputted from the optical modulating device contains the light having the same frequency as that of the incident light.

What is claimed is:

1. An optical measuring instrument comprising:
   optical multiplexing means for multiplexing incident light;
   light emitting means for emitting the light having a short coherence length;
   optical demultiplexing means for demultiplexing the light emitted by said light emitting means into a measurement light beam and first through N-th reference light beams;
   reference light introducing means for modulating the first through N-th reference light beams demultiplexed by said optical demultiplexing means in patterns different from each other and introducing the thus modulated first through N-th reference light beams to the optical multiplexing means;
   measurement light introducing means for introducing the measurement light demultiplexed by said optical demultiplexing means to a measurement object sample and introducing the measurement light reflected and scattered within by the measurement object sample to said optical multiplexing means;
   photoelectric converting means for outputting an electric signal assuming a level corresponding to an intensity of the light multiplexed by said optical multiplexing means; and
   calculating means for calculating optical characteristic data about first through N-th measuring points existing in positions corresponding to lengths of optical paths extending from said optical demultiplexing means of the first through N-th reference light beams to said optical multiplexing means at that point of time within the measurement object sample from the electric signals outputted by said photoelectric converting means on the basis of patterns of modulation effected on the first through N-th reference light beams by the reference light introducing means.

2. An optical measuring instrument as claimed in claim 1, characterized in that said reference light introducing means comprises:
   first through N-th reflectors provided in positions upon which the first through N-th reference light beams demultiplexed by said optical demultiplexing means is incident;
   introducing means for introducing to said optical multiplexing means the first through N-th reference light beams reflected by said first through N-th reflectors; and
   reflector position control means for modulating the first through N-th reference light beams in patterns different from each other by controlling positions of said first through N-th reflectors.

3. An optical measuring instrument as claimed in claim 2, characterized in that
   said first through N-th reflectors are reflectors of which side surfaces receive incidences of the reference light beams, each having a rotary shaft and assuming such configuration that a distance of the side surface upon which the reference light beam is incident from the center of the rotary shaft changes corresponding to an angle of rotation of the rotary shaft, and in that
   said reflector position control means controls the angle of rotation of the rotary shaft.

4. An optical measuring instrument as claimed in claim 2, characterized in that
   said first through N-th reflectors are reflectors, fixed to the same rotary shaft, of which side surfaces receive incidences of the reference light beams, each assuming such a configuration that a distance of the side surface upon which the reference light beam is incident from the center of the rotary shaft changes corresponding to the angle of the rotation of the rotary shaft besides at a rate different from rates of the changes in the distance of other reflectors, and in that
   said reflector position control means controls the angle of rotation of the rotary shaft.

5. An optical measuring instrument as claimed in claim 1, characterized in that said reference light introducing means comprises:
   first through N-th reflectors fixed to a fixing member having the rotary shaft so that the distances thereof from the rotary shaft are different from each other;
   introducing means for introducing to said optical multiplexing means the first through N-th reference light beams reflected by said first through N-th reflectors; and
   reflector position control means for modulating the first through N-th reference light beams in the patterns different from each other by controlling the angle of rotation of the rotary shaft.

6. An optical measuring instrument as claimed in claim 5, characterized in that said first through N-th reflectors are cylindrical mirrors.

7. An optical measuring instrument as claimed in claim 5, characterized in that
   said first through N-th reflectors are rotatably fitted to said fixing member, and in that
   said reflector position control means controls a position of the fixing member and controls angles of said first through N-th reflectors to said fixing member so that reflecting surfaces of said first through N-th reflectors are directed in a direction corresponding to a tilt of said fixing member.

8. An optical measuring instrument as claimed in claim 1, characterized in that said reference light introducing means comprises:
   first through N-th optical fibers for introducing to said optical multiplexing means the first through N-th reference light beams demultiplexed by said optical demultiplexing means, said optical fibers being partially wound on first through N-th electrostrictive elements; and
   electrostrictive element control means for controlling said first through N-th electrostrictive elements so as to modulate the first through N-th reference light beams in the patterns different from each other.

9. An optical measuring instrument as claimed in claim 1, characterized in that said reference light introducing means includes an acousto-optic element for modulating the reference light beam.

10. An optical measuring instrument as claimed in claim 1, characterized in that said reference light introducing means comprises:
    optical media exhibiting a distribution of refractive indexes and provided on optical paths of the first through N-th reference light beams; and optical medium position control means for modulating the first through N-th reference light beams in the patterns different from each other by changing relative positions of the optical media with respect to the optical paths of the first through N-th reference light beams.

11. An optical measuring instrument comprising:

optical multiplexing means for multiplexing incident light;

light emitting means for emitting first through N-th light beams having a short coherence length and wavelengths different from each other;

optical demultiplexing means for generating first through N-th reference light beams and first through N-th measurement light beams by demultiplexing the first through N-th light beams emitted by said light emitting means into reference light beams and measurement light beams;

reference light introducing means for modulating the first through N-th reference light beams generated by said optical demultiplexing means and introducing these reference light beams to said optical multiplexing means;

measurement light introducing means for introducing the first through N-th measurement light beams demultiplexed by said optical demultiplexing means to one point of a measurement object sample and introducing to said optical multiplexing means the first through N-th measurement light beams reflected and scattered within by the measurement object sample;

photoelectric converting means for outputting an electric signal assuming a level corresponding to an intensity of the light multiplexed by said optical multiplexing means; and calculating means for calculating optical characteristic data about first through N-th measuring points existing in positions corresponding to lengths of optical paths extending from said optical demultiplexing means of the first through N-th reference light beams to said optical multiplexing means at that point of time within the measurement object sample from the electric signals outputted by said photoelectric converting means by use of patterns of modulation effected on the first through N-th reference light beams by said reference light introducing means and information on wavelength of the first through N-th reference light beams.

12. An optical measuring instrument as claimed in claim 1, characterized in that said reference light introducing means maintains, when said calculating means obtains the electric signals for calculating the optical characteristic data, a state where a variation width of each of the optical paths of the first through N-th reference light beams which extend from said optical demultiplexing means of the first through N-th reference light beams to said optical multiplexing means becomes approximately a coherent light length, or under, of the light emitted by said light emitting means.

13. An optical measuring instrument as claimed in claim 12, characterized by further comprising reference light optical path length changing means for changing the lengths of the optical paths of the first through N-th reference light beams.

14. An optical measuring instrument as claimed in claim 12, characterized in that said reference light introducing means performs on the first through N-th reference light beams a frequency modulation in a configuration of sine wave with an amplitude being set so that a DC component contained in the electric signal outputted by said photoelectric converting means becomes "0".

15. An optical measuring instrument as claimed in claim 1, further comprising detecting means for detecting a modulation pattern given to each of the reference light beams by said reference light introducing means, characterized in that said calculating means calculates the optical characteristic data about the first through N-th measuring points by use of the electric signals outputted by said photoelectric converting means and a result of the detection by said detecting means.

16. An optical measuring instrument as claimed in claim 1, further comprising:

measurement light introducing position changing means for changing a position to which said measurement light introducing means introduce the measurement light; and storing means for storing introducing position information defined as information indicating the introducing position in such a form that a use order is recognizable, characterized in that said calculating means calculates the optical characteristic data about the respective measuring points on which the introducing position information is stored in said storing means by controlling said measurement light introducing position changing means on the basis of the position information stored in said storing means.

17. An optical measuring instrument as claimed in claim 16, characterized in that said storing means stores the introducing position information and measuring time information in such a form that the use order is recognizable, and in that said calculating means calculates the optical characteristic data by using the electric signals outputted by said photoelectric converting means for a time corresponding to the measuring time information corresponding to each of the measuring points with respect to the measuring points on which the introducing position information is stored in said storing means.

18. An optical measuring instrument comprising:

optical multiplexing means for multiplexing incident light;

light emitting means for emitting the light having a short coherence length;

optical demultiplexing means for demultiplexing the light emitted by said light emitting means into a measurement light beam and reference light beams;

reference light modulating means for generating modulation reference light beams, by utilizing multi-reflections of the reference light, containing a plurality of light components of which frequencies and optical path lengths to positions of being introduced by said optical multiplexing means are different from each other on the basis of the reference light beams demultiplexed by said optical demultiplexing means, and for introducing the modulation reference light beams to said optical multiplexing means;

measurement light introducing means for introducing the measurement light beams demultiplexed by said optical demultiplexing means into the measurement object sample and for introducing the measurement light beams reflected and scattered within by the measurement object sample to said optical multiplexing means;

photoelectric converting means for outputting an electric signal assuming a level corresponding to an intensity of the light multiplexed by said optical multiplexing means; and calculating means for calculating optical characteristic data about a plurality of measuring points within the measurement object sample from the electric signals outputted by said photoelectric converting means on the basis of frequencies and lengths of the optical path extending from the light emitting means to the optical multiplexing means of a plurality of optical components contained in the modulation reference light beams.

19. An optical measuring instrument as claimed in claim 18, characterized in that said reference light modulating means comprise:

a half-mirror upon which the reference light is incident;

a total reflection mirror for reflecting the light penetrating said half-mirror to make this beam of light travel back to said half-mirror;

moving means for moving said half-mirror or said total reflection mirror in a direction of its normal line; and modulation reference light introducing means for introducing the light returned by said total reflection mirror and penetrating said half-mirror as modulation reference light to said optical multiplexing means.

20. An optical measuring instrument as claimed in claim 18, characterized in that said reference light modulating means comprise:

a half-mirror upon which the reference light is incident;

a first total reflection mirror for reflecting the light penetrating said half-mirror to make this beam of light travel back to said half-mirror;

a second total reflection mirror for returning to said half-mirror the reflected light, by said half-mirror, of the light coming from said first total reflection;

moving means for moving said first total reflection mirror in a direction of its normal line; and modulation reference light introducing means for introducing the light returned to said half-mirror by said first total reflection mirror and penetrating said half-mirror as modulation reference light to said optical multiplexing means.

21. An optical measuring instrument as claimed in claim 18, characterized in that said reference light modulating means comprise:

a half-mirror upon which the reference light is incident;

a first total reflection mirror for reflecting the light penetrating said half-mirror to make this beam of light travel back to said half-mirror;

a second total reflection mirror for returning to said half-mirror the reflected light, by said half-mirror, of the light coming from said first total reflection;

moving means for moving said second total reflection mirror in a direction of its normal line;

and modulation reference light introducing means for introducing the light returned to said half-mirror by said first total reflection mirror and penetrating said half-mirror as modulation reference light to said optical multiplexing means.

* * * * *